(12) United States Patent
Abbracchio et al.

(10) Patent No.: US 8,158,593 B2
(45) Date of Patent: Apr. 17, 2012

(54) GPR17 MODULATORS, METHOD OF SCREENING AND USES THEREOF

(75) Inventors: Maria Pia Abbracchio, Milan (IT); Paolo Ciana, Gravellona Toce (IT); Gianenrico Rovati, Pavia (IT); Claudia Martini, Pisa (IT); Maria Letizia Trincavelli, Pontedera (IT); Claudia Verderio, Milan (IT)

(73) Assignees: Universita' degli Studi di Milano, Milan (IT); Universita' degli Studi di Pisa, Pisa (IT); Consiglio Nazionale delle Ricerche, Rome (IT)

( * ) Notice: Subject to any disclaimer, the term of this patent is extended or adjusted under 35 U.S.C. 154(b) by 430 days.

(21) Appl. No.: 11/665,835

(22) PCT Filed: Oct. 17, 2005

(86) PCT No.: PCT/EP2005/011157
§ 371 (c)(1),
(2), (4) Date: Jun. 11, 2007

(87) PCT Pub. No.: WO2006/045476
PCT Pub. Date: May 4, 2006

(65) Prior Publication Data
US 2009/0156521 A1   Jun. 18, 2009

(30) Foreign Application Priority Data
Oct. 21, 2004 (IT) ............................. MI2004A2007

(51) Int. Cl.
*C12N 15/11* (2006.01)
*C12Q 1/68* (2006.01)
*C12N 5/00* (2006.01)
*C07H 21/04* (2006.01)

(52) U.S. Cl. ........ 514/44 A; 435/6.1; 435/325; 435/375; 536/23.1; 536/24.5

(58) Field of Classification Search ................. None
See application file for complete search history.

(56) References Cited

U.S. PATENT DOCUMENTS

| 5,759,804 A | * | 6/1998 | Godiska et al. | ............. 435/69.1 |
| 2002/0052001 A1 | | 5/2002 | Cousens et al. | |

FOREIGN PATENT DOCUMENTS

| WO | 96/39438 | | 12/1996 |
| WO | 01/68842 | | 9/2001 |
| WO | WO 01/68842 | * | 9/2001 |
| WO | 2005/040829 | | 5/2005 |

OTHER PUBLICATIONS

Abbracchio M P et al: "Characteriszation of the UDP-glucose receptor (re-named her the P2V14 receptor) adds diversity to the P2Y receptor family" Trends in Pharmacological Sciences, Elsevier, Amsterdam, NL, vol. 24, No. 2, Feb. 2003, pp. 52-55, XP004404389.
Wang Yun et al: "Diadenosine tetraphosphate protects against injuries induced by ischemia and 6-hydroxydopamine in rat brain." The Journal of the Society for Neuroscience: The Official Journal of the Society for Neuroscience. Aug. 27, 2003, vol. 23, No. 21, Aug. 27, 2003, pp. 7958-7965, XP002365766.

* cited by examiner

*Primary Examiner* — Doug Schultz
(74) *Attorney, Agent, or Firm* — Young & Thompson

(57) ABSTRACT

The invention provides GPR17 modulators, methods of screening and use thereof for diagnosis and therapy of diseases or dysfunctions involving GPR17 activation, particularly ischemic brain damage.

15 Claims, 9 Drawing Sheets

Figure 1.1

```
1    ATGAATCGCCTTGAAGTGGCTCCCCCAGGTCTGATCACCAACTTCTCCCTGGCCACGGCAGAGCAATGTGGCCAGGAGACGCCACTGGAG  90
     M  N  G  L  E  V  A  P  P  G  L  I  T  N  F  S  L  A  T  A  E  Q  C  G  Q  E  T  P  L  E
                                                                                      *
91   AACATGCTGTTCGCCTCCTTCTACCTTCTGGATTTTATCCTGGCTTTAGTTGGCAATACCCTGGCTCTGTGGCTTTTCATCCGAGACCAC 180
     N  M  L  F  A  S  F  Y  L  L  D  F  I  L  A  L  V  G  N  T  L  A  L  W  L  F  I  R  D  H
        S                                                            TM1
181  AAGTCCGGGACCCCGGCCAACGTGTTCCTGATGCATCTGGCCGTGGCCGACTTGTCGTGCGTGCTGGTCCTGCCCACCCGCCTGGTCTAC 270
     K  S  G  T  P  A  N  V  F  L  M  H  L  A  V  A  D  L  S  C  V  L  V  L  P  T  R  L  V  Y
                                                              TM2
271  CACTTCTCTGGGAACCACTGGCCATTTGGGGAAATCGCATGCCGTCTCACCGGCTTCCTCTTTTACCTCAACATGTACGCCAGCATCTAC 360
     H  F  S  G  N  H  W  P  F  G  E  I  A  C  R  L  T  G  F  L  F  Y  L  N  M  Y  A  S  I  Y
                                                                                      TM3
361  TTCCTCACCTGCATCAGCGCCGACCGTTTCCTGGCCATTGTGCACCCGGTCAAGTCCCTCAAGCTCCGCAGGCCCCTCTACGCACACCTG 450
     F  L  T  C  I  S  A  D  R  F  L  A  I  V  H  P  V  K  S  L  K  L  R  R  P  L  Y  A  H  L
451  GCCTGTGCCTTCCTGTGGTGGTGGTGGCTGTGGCCATGGCCCCGCTGCTGGTGAGCCCACAGACCGTGCAGACCAACCACACGGTGGTC 540
     A  C  A  F  L  W  V  V  V  A  V  A  M  A  P  L  L  V  S  P  Q  T  V  Q  T  N  H  T  V  V
                    TM4
541  TGCCTGCAGCTGTACCGGGAGAAGGCCTCCCACCATGCCCTGGTGTCCCTGGCAGTGGCCTTCACCTTCCCCTTCATCACCACGGTCACC 630
     C  L  Q  L  Y  R  E  K  A  S  H  H  A  L  V  S  L  A  V  A  F  T  F  P  F  I  T  T  V  T
                                  *                                                   TM5
631  TGCTACCTGCTGATCATCCGCAGCCTGCGGCAGGGCCTGCGTGTGGAGAAGCGCCTTAAGACCAACGCAGTGCGCATGATCGCCATAGTG 720
     C  Y  L  L  I  I  R  S  L  R  Q  G  L  R  V  E  K  R  L  K  T  N  A  V  R  M  I  A  I  V
721  TTGGCCATCTTCCTGGTCTGCTTCGTGCCCTACCACGTCAACCGCTCCGTCTACGTGCTGCACTACCGCAGCCATGGGGCCTCCTGCGCC 810
     L  A  I  F  L  V  C  F  V  P  Y  H  V  N  R  S  V  Y  V  L  H  Y  R  S  M  G  A  S  C  A
                TM6             S
811  ACCCAGCGCATCCTGGCCCTGGCAAACCGCATCACCTCCTGCCTCACCAGCCTCAACGGGGCACTCGACCCCATCATGTATTTCTTCGTG 900
     T  Q  R  I  L  A  L  A  N  R  I  T  S  C  L  T  S  L  N  G  A  L  D  P  I  M  Y  F  F  V
                          *                                    TM7
901  GCTGAGAAGTTCCGGCCACGCCCTGTGCAACTTGCTCTGTGGCAAAAGGCTCAAGGGCCCGCCCCCCAGCTTCGAAGGGAAAACCAACGAG 990
     A  E  K  F  R  H  A  L  C  N  L  L  C  G  K  R  L  K  G  P  P  P  S  F  E  G  K  T  N  E
                                                                            *
991  AGCTCGCTGAGTGCCAAGTCAGAGCTGTGA 1020/SEQ ID NO 8
     S  S  L  S  A  K  S  E  L  * /SEQ ID NO 9
     *           *
```

Figure 2.1

Figure 3.1
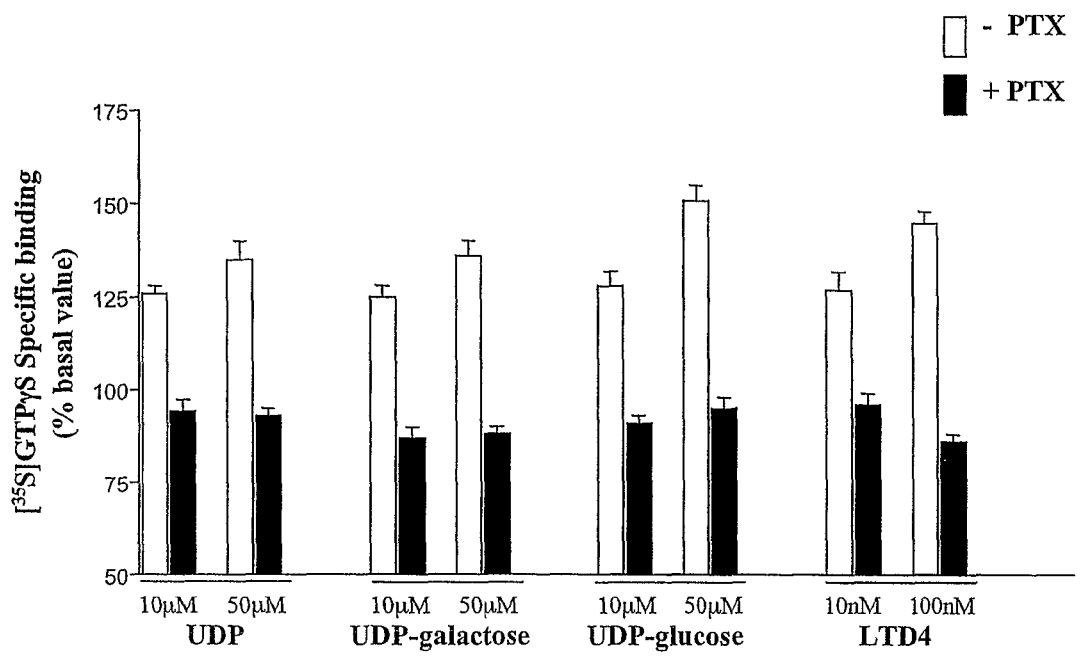

Figure 4.1
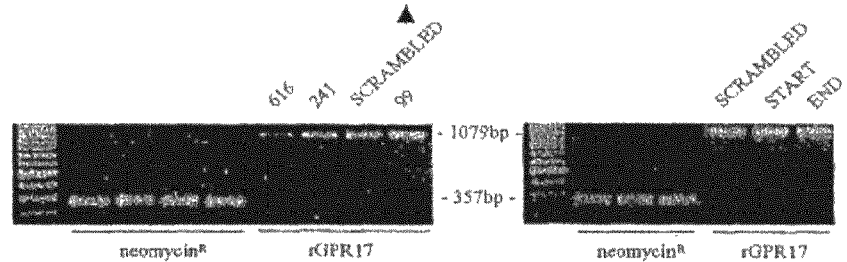

SEQUENCE LISTING

<160> NUMBER OF SEQ ID NOS: 21

<210> SEQ ID NO 1
<211> LENGTH: 20
<212> TYPE: DNA
<213> ORGANISM: Rattus norvegicus

<400> SEQUENCE: 1
aactgtaccg ggagaaggcc                                           20

<210> SEQ ID NO 2
<211> LENGTH: 19
<212> TYPE: DNA
<213> ORGANISM: Rattus norvegicus

<400> SEQUENCE: 2
gggatcacaa gtcaggcac                                            19

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
gactccagcc aaagcatgaa                                           20

<210> SEQ ID NO 4
<211> LENGTH: 21

```
<212> TYPE: DNA
<213> ORGANISM: Artificial Sequence
<220> FEATURE:
<223> OTHER INFORMATION: synthetic oligonucleotide

<400> SEQUENCE: 4
gggtctgctg agtcctaaac a                                              21

<210> SEQ ID NO 5
<211> LENGTH: 339
<212> TYPE: PRT
<213> ORGANISM: Homo sapiens

<400> SEQUENCE: 5
```

| Met | Asn | Gly | Leu | Glu | Val | Ala | Pro | Pro | Gly | Leu | Ile | Thr | Asn | Phe | Ser |
|---|---|---|---|---|---|---|---|---|---|---|---|---|---|---|---|
| 1 | | | | 5 | | | | | 10 | | | | | 15 | |

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
            260                 265                 270

Arg Ile Leu Ala Leu Ala Asn Arg Ile Thr Ser Cys Leu Thr Ser Leu
        275                 280                 285

Asn Gly Ala Leu Asp Pro Ile Met Tyr Phe Phe Val Ala Glu Lys Phe
290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu

<210> SEQ ID NO 6
<211> LENGTH: 339
<212> TYPE: PRT
<213> ORGANISM: Mus musculus

<400> SEQUENCE: 6

```
Met Asn Gly Leu Glu Ala Ala Leu Pro Ser Leu Thr Asp Asn Ser Ser
 1               5                  10                  15

Leu Ala Tyr Ser Glu Gln Cys Gly Gln Glu Thr Pro Leu Glu Asn Met
            20                  25                  30

Leu Phe Ala Cys Phe Tyr Leu Leu Asp Phe Ile Leu Ala Phe Val Gly
        35                  40                  45

Asn Ala Leu Ala Leu Trp Leu Phe Ile Trp Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Pro Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Ile Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Ala Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Pro Arg
    210                 215                 220

Ile Glu Lys His Leu Lys Asn Lys Ala Val Arg Met Ile Ala Met Val
225                 230                 235                 240

Leu Ala Ile Phe Leu Ile Cys Phe Val Pro Tyr His Ile His Arg Ser
                245                 250                 255

Val Tyr Val Leu His Tyr Arg Gly Gly Gly Thr Ser Cys Ala Ala Gln
            260                 265                 270

Arg Ala Leu Ala Leu Gly Asn Arg Ile Thr Ser Cys Leu Thr Ser Leu
        275                 280                 285

Asn Gly Ala Leu Asp Pro Val Met Tyr Phe Phe Val Ala Glu Lys Phe
    290                 295                 300

Arg His Ala Leu Cys Asn Leu Leu Cys Ser Lys Arg Leu Thr Gly Pro
305                 310                 315                 320

Pro Pro Ser Phe Glu Gly Lys Thr Asn Glu Ser Ser Leu Ser Ala Arg
                325                 330                 335

Ser Glu Leu
```

<210> SEQ ID NO 7
<211> LENGTH: 339
<212> TYPE: PRT
<213> ORGANISM: Rattus norvegicus

<400> SEQUENCE: 7

```
Met Asp Gly Leu Glu Thr Ala Leu Pro Ser Leu Thr Asp Asn Ala Ser
1               5                   10                  15
Leu Ala Tyr Ser Glu Gln Cys Gly Gln Glu Thr Pro Leu Glu Asn Met
            20                  25                  30
Leu Phe Ala Cys Phe Tyr Leu Leu Asp Phe Ile Leu Ala Phe Val Gly
        35                  40                  45
Asn Ala Leu Ala Leu Trp Leu Phe Ile Trp Asp His Lys Ser Gly Thr
    50                  55                  60
Pro Ala Asn Val Phe Leu Met His Leu Ala Val Ala Asp Leu Ser Cys
65                  70                  75                  80
Val Leu Val Leu Pro Thr Arg Leu Val Tyr His Phe Ser Gly Asn His
                85                  90                  95
Trp Pro Phe Gly Glu Ile Pro Cys Arg Leu Thr Gly Phe Leu Phe Tyr
            100                 105                 110
Leu Asn Met Tyr Ala Ser Ile Tyr Phe Leu Thr Cys Ile Ser Ala Asp
        115                 120                 125
Arg Phe Leu Ala Ile Val His Pro Val Lys Ser Leu Lys Leu Arg Arg
    130                 135                 140
Pro Leu Tyr Ala His Leu Ala Cys Ala Phe Leu Trp Ile Val Val Ala
145                 150                 155                 160
Val Ala Met Ala Pro Leu Leu Val Ser Pro Gln Thr Val Gln Thr Asn
                165                 170                 175
His Thr Val Val Cys Leu Gln Leu Tyr Arg Glu Lys Ala Ser His His
            180                 185                 190
Ala Leu Ala Ser Leu Ala Val Ala Phe Thr Phe Pro Phe Ile Thr Thr
        195                 200                 205
Val Thr Cys Tyr Leu Leu Ile Ile Arg Ser Leu Arg Gln Gly Pro Arg
    210                 215                 220
Ile Glu Lys His Leu Lys Asn Lys Ala Val Arg Met Ile Ala Met Val
225                 230                 235                 240
Leu Ala Ile Phe Leu Ile Cys Phe Val Pro Tyr His Ile His Arg Ser
                245                 250                 255
Val Tyr Val Leu His Tyr Arg Gly Gly Gly Thr Ser Cys Ser Ala Gln
            260                 265                 270
Arg Ala Leu Ala Leu Gly Asn Arg Ile Thr Ser Cys Leu Thr Ser Leu
        275                 280                 285
Asn Gly Ala Leu Asp Pro Val Met Tyr Phe Phe Val Ala Glu Lys Phe
    290                 295                 300
Arg His Ala Leu Cys Asn Leu Leu Cys Ser Lys Arg Leu Thr Gly Pro
305                 310                 315                 320
Pro Pro Ser Phe Glu Gly Lys Thr Asn Glu Ser Ser Leu Ser Ala Arg
                325                 330                 335
Ser Glu Leu
```

<210> SEQ ID NO 8
<211> LENGTH: 1020
<212> TYPE: DNA
<213> ORGANISM: Homo sapiens

<400> SEQUENCE: 8

```
atgaatggcc ttgaagtggc tcccccaggt ctgatcacca acttctccct ggccacggca    60
gagcaatgtg gccaggagac gccactggag aacatgctgt tcgcctcctt ctaccttctg   120
```

-continued

```
gattttatcc tggctttagt tggcaatacc ctggctctgt ggcttttcat ccgagaccac    180
aagtccggga ccccggccaa cgtgttcctg atgcatctgg ccgtggccga cttgtcgtgc    240
gtgctggtcc tgcccacccg cctggtctac cacttctctg ggaaccactg gccatttggg    300
gaaatcgcat gccgtctcac cggcttcctc ttctacctca acatgtacgc cagcatctac    360
ttcctcacct gcatcagcgc cgaccgtttc ctggccattg tgcacccggt caagtccctc    420
aagtccgcag gcccctcta cgcacacctg gcctgtgcct tcctgtgggt ggtggtggct    480
gtggccatgg cccgctgct ggtgagccca cagaccgtgc agaccaacca cacggtggtc    540
tgcctgcagc tgtaccggga aaggcctcc caccatgccc tggtgtccct ggcagtggcc    600
ttcaccttcc cgttcatcac cacggtcacc tgctacctgc tgatcatccg cagcctgcgg    660
cagggcctgc gtgtggagaa gcgcctcaag accaaggcag tgcgcatgat cgccatagtg    720
ctggccatct tcctggtctg cttcgtgccc taccacgtca accgctccgt ctacgtgctg    780
cactaccgca gccatggggc ctcctgcgcc acccagcgca tcctggccct ggcaaaccgc    840
atcacctcct gcctcaccag cctcaacggg gcactcgacc ccatcatgta tttcttcgtg    900
gctgagaagt tccgccacgc cctgtgcaac ttgctctgtg gcaaaaggct caagggcccg    960 cccccccagct tcgaagggaa aaccaacgag agctcgctga gtgccaagtc agagctgtga    1020
```

<210> SEQ ID NO 9
<211> LENGTH: 339
<212> TYPE: PRT
<213> ORGANISM: Homo sapiens

<400> SEQUENCE: 9

```
Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
                20                  25                  30

Leu Phe Ala Ser Phe Tyr Leu Leu Asp Phe Ile Leu Ala Leu Val Gly
            35                  40                  45

Asn Thr Leu Ala Leu Trp Leu Phe Ile Arg Asp His Lys Ser Gly Thr
        50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220
```

```
Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
            245                 250                 255

Val Tyr Val Leu His Tyr Arg Ser His Gly Ala Ser Cys Ala Thr Gln
        260                 265                 270

Arg Ile Leu Ala Leu Ala Asn Arg Ile Thr Ser Cys Leu Thr Ser Leu
    275                 280                 285

Asn Gly Ala Leu Asp Pro Ile Met Tyr Phe Phe Val Ala Glu Lys Phe
    290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
            325                 330                 335

Ser Glu Leu

<210> SEQ ID NO 10
<211> LENGTH: 373
<212> TYPE: PRT
<213> ORGANISM: Homo sapiens

<400> SEQUENCE: 10

Met Thr Glu Val Leu Trp Pro Ala Val Pro Asn Gly Thr Asp Ala Ala
1               5                   10                  15

Phe Leu Ala Gly Pro Gly Ser Ser Trp Gly Asn Ser Thr Val Ala Ser
            20                  25                  30

Thr Ala Ala Val Ser Ser Ser Phe Lys Cys Ala Leu Thr Lys Thr Gly
        35                  40                  45

Phe Gln Phe Tyr Tyr Leu Pro Ala Val Tyr Ile Leu Val Phe Ile Ile
    50                  55                  60

Gly Phe Leu Gly Asn Ser Val Ala Ile Trp Met Phe Val Phe His Met
65                  70                  75                  80

Lys Pro Trp Ser Gly Ile Ser Val Tyr Met Phe Asn Leu Ala Leu Ala
                85                  90                  95

Asp Phe Leu Tyr Val Leu Thr Leu Pro Ala Leu Ile Phe Tyr Tyr Phe
            100                 105                 110

Asn Lys Thr Asp Trp Ile Phe Gly Asp Ala Met Cys Lys Leu Gln Arg
        115                 120                 125

Phe Ile Phe His Val Asn Leu Tyr Gly Ser Ile Leu Phe Leu Thr Cys
    130                 135                 140

Ile Ser Ala His Arg Tyr Ser Gly Val Val Tyr Pro Leu Lys Ser Leu
145                 150                 155                 160

Gly Arg Leu Lys Lys Lys Asn Ala Ile Cys Ile Ser Val Leu Val Trp
                165                 170                 175

Leu Ile Val Val Val Ala Ile Ser Pro Ile Leu Phe Tyr Ser Gly Thr
            180                 185                 190

Gly Val Arg Lys Asn Lys Thr Ile Thr Cys Tyr Asp Thr Thr Ser Asp
        195                 200                 205

Glu Tyr Leu Arg Ser Tyr Phe Ile Tyr Ser Met Cys Thr Thr Val Ala
    210                 215                 220

Met Phe Cys Val Pro Leu Val Leu Ile Leu Gly Cys Tyr Gly Leu Ile
225                 230                 235                 240

Val Arg Ala Leu Ile Tyr Lys Asp Leu Asp Asn Ser Pro Leu Arg Arg
                245                 250                 255

Lys Ser Ile Tyr Leu Val Ile Ile Val Leu Thr Val Phe Ala Val Ser
```

-continued

```
                260                 265                 270
Tyr Ile Pro Phe His Val Met Lys Thr Met Asn Leu Arg Ala Arg Leu
        275                 280                 285
Asp Phe Gln Thr Pro Ala Met Cys Ala Phe Asn Asp Arg Val Tyr Ala
        290                 295                 300
Thr Tyr Gln Val Thr Arg Gly Leu Ala Ser Leu Asn Ser Cys Val Asp
305                 310                 315                 320
Pro Ile Leu Tyr Phe Leu Ala Gly Asp Thr Phe Arg Arg Arg Leu Ser
                325                 330                 335
Arg Ala Thr Arg Lys Ala Ser Arg Arg Ser Glu Ala Asn Leu Gln Ser
                340                 345                 350
Lys Ser Glu Asp Met Thr Leu Asn Ile Leu Pro Glu Phe Lys Gln Asn
                355                 360                 365
Gly Asp Thr Ser Leu
        370

<210> SEQ ID NO 11
<211> LENGTH: 377
<212> TYPE: PRT
<213> ORGANISM: Homo sapiens

<400> SEQUENCE: 11

Met Ala Ala Asp Leu Gly Pro Trp Asn Asp Thr Ile Asn Gly Thr Trp
1               5                   10                  15
Asp Gly Asp Glu Leu Gly Tyr Arg Cys Arg Phe Asn Glu Asp Phe Lys
                20                  25                  30
Tyr Val Leu Leu Pro Val Ser Tyr Gly Val Val Cys Val Pro Gly Leu
        35                  40                  45
Cys Leu Asn Ala Val Ala Leu Tyr Ile Phe Leu Cys Arg Leu Lys Thr
    50                  55                  60
Trp Asn Ala Ser Thr Thr Tyr Met Phe His Leu Ala Val Ser Asp Ala
65                  70                  75                  80
Leu Tyr Ala Ala Ser Leu Pro Leu Leu Val Tyr Tyr Ala Arg Gly
                85                  90                  95
Asp His Trp Pro Phe Ser Thr Val Leu Cys Lys Leu Val Arg Phe Leu
                100                 105                 110
Phe Tyr Thr Asn Leu Tyr Cys Ser Ile Leu Phe Leu Thr Cys Ile Ser
                115                 120                 125
Val His Arg Cys Leu Gly Val Leu Arg Pro Leu Arg Ser Leu Arg Trp
        130                 135                 140
Gly Arg Ala Arg Tyr Ala Arg Arg Val Ala Gly Ala Val Trp Val Leu
145                 150                 155                 160
Val Leu Ala Cys Gln Ala Pro Val Leu Tyr Phe Val Thr Thr Ser Ala
                165                 170                 175
Arg Gly Gly Arg Val Thr Cys His Asp Thr Ser Ala Pro Glu Leu Phe
                180                 185                 190
Ser Arg Phe Val Ala Tyr Ser Ser Val Met Leu Gly Leu Leu Phe Ala
                195                 200                 205
Val Pro Phe Ala Val Ile Leu Val Cys Tyr Val Leu Met Ala Arg Arg
        210                 215                 220
Leu Leu Lys Pro Ala Tyr Gly Thr Ser Gly Gly Leu Pro Arg Ala Lys
225                 230                 235                 240
Arg Lys Ser Val Arg Thr Ile Ala Val Val Leu Ala Val Phe Ala Leu
                245                 250                 255
Cys Phe Leu Pro Phe His Val Thr Arg Thr Leu Tyr Tyr Ser Phe Arg
```

```
                    260                 265                 270
Ser Leu Asp Leu Ser Cys His Thr Leu Asn Ala Ile Asn Met Ala Tyr
        275                 280                 285
Lys Val Thr Arg Pro Leu Ala Ser Ala Asn Ser Cys Leu Asp Pro Val
        290                 295                 300
Leu Tyr Phe Leu Ala Gly Gln Arg Leu Val Arg Phe Ala Arg Asp Ala
305                 310                 315                 320
Lys Pro Pro Thr Gly Pro Ser Pro Ala Thr Pro Ala Arg Arg Arg Leu
                325                 330                 335
Gly Leu Arg Arg Ser Asp Arg Thr Asp Met Gln Arg Ile Glu Asp Val
                340                 345                 350
Leu Gly Ser Ser Glu Asp Ser Arg Arg Thr Glu Ser Thr Pro Ala Gly
                355                 360                 365
Ser Glu Asn Thr Lys Asp Ile Arg Leu
                370                 375

<210> SEQ ID NO 12
<211> LENGTH: 365
<212> TYPE: PRT
<213> ORGANISM: Homo sapiens

<400> SEQUENCE: 12

Met Ala Ser Thr Glu Ser Ser Leu Leu Arg Ser Leu Gly Leu Ser Pro
1               5                   10                  15
Gly Pro Gly Ser Ser Glu Val Glu Leu Asp Cys Trp Phe Asp Glu Asp
                20                  25                  30
Phe Lys Phe Ile Leu Leu Pro Val Ser Tyr Ala Val Val Phe Val Leu
            35                  40                  45
Gly Leu Gly Leu Asn Ala Pro Thr Leu Trp Leu Phe Ile Phe Arg Leu
        50                  55                  60
Arg Pro Trp Asp Ala Thr Ala Thr Tyr Met Phe His Leu Ala Leu Ser
65                  70                  75                  80
Asp Thr Leu Tyr Val Leu Ser Leu Pro Thr Leu Ile Tyr Tyr Tyr Ala
                85                  90                  95
Ala His Asn His Trp Pro Phe Gly Thr Glu Ile Cys Lys Phe Val Arg
                100                 105                 110
Phe Leu Phe Tyr Trp Asn Leu Tyr Cys Ser Val Leu Phe Leu Thr Cys
            115                 120                 125
Ile Ser Val His Arg Tyr Leu Gly Ile Cys His Pro Leu Arg Ala Leu
        130                 135                 140
Arg Trp Gly Arg Pro Arg Leu Ala Gly Leu Leu Cys Leu Ala Val Trp
145                 150                 155                 160
Leu Val Val Ala Gly Cys Leu Val Pro Asn Leu Phe Phe Val Thr Thr
                165                 170                 175
Ser Asn Lys Gly Thr Thr Val Leu Cys His Asp Thr Thr Arg Pro Glu
                180                 185                 190
Glu Phe Asp His Tyr Val His Phe Ser Ser Ala Val Met Gly Leu Leu
            195                 200                 205
Phe Gly Val Pro Cys Leu Val Thr Leu Val Cys Tyr Gly Leu Met Ala
        210                 215                 220
Arg Arg Leu Tyr Gln Pro Leu Pro Gly Ser Ala Gln Ser Ser Ser Arg
225                 230                 235                 240
Leu Arg Ser Leu Arg Thr Ile Ala Val Val Leu Thr Val Phe Ala Val
                245                 250                 255
Cys Phe Val Pro Phe His Ile Thr Arg Thr Ile Tyr Tyr Leu Ala Arg
```

```
                   260                 265                 270
Leu Leu Glu Ala Asp Cys Arg Val Leu Asn Ile Val Asn Val Tyr
                275                 280                 285
Lys Val Thr Arg Pro Leu Ala Ser Ala Asn Ser Cys Leu Asp Pro Val
            290                 295                 300
Leu Tyr Leu Leu Thr Gly Asp Lys Tyr Arg Arg Gln Leu Arg Gln Leu
305                 310                 315                 320
Cys Gly Gly Gly Lys Pro Gln Pro Arg Thr Ala Ala Ser Ser Leu Ala
                325                 330                 335
Leu Val Ser Leu Pro Glu Asp Ser Ser Cys Arg Trp Ala Ala Thr Pro
            340                 345                 350
Gln Asp Ser Ser Cys Ser Thr Pro Arg Ala Asp Arg Leu
                355                 360                 365

<210> SEQ ID NO 13
<211> LENGTH: 328
<212> TYPE: PRT
<213> ORGANISM: Homo sapiens

<400> SEQUENCE: 13

Met Glu Trp Asp Asn Gly Thr Gly Gln Ala Leu Gly Leu Pro Pro Thr
1               5                   10                  15
Thr Cys Val Tyr Arg Glu Asn Phe Lys Gln Leu Leu Leu Pro Pro Val
            20                  25                  30
Tyr Ser Ala Val Leu Ala Ala Gly Leu Pro Leu Asn Ile Cys Val Ile
        35                  40                  45
Thr Gln Ile Cys Thr Ser Arg Arg Ala Leu Thr Arg Thr Ala Val Tyr
    50                  55                  60
Thr Leu Asn Leu Ala Leu Ala Asp Leu Leu Tyr Ala Cys Ser Leu Pro
65                  70                  75                  80
Leu Leu Ile Tyr Asn Tyr Ala Gln Gly Asp His Trp Pro Phe Gly Asp
                85                  90                  95
Phe Ala Cys Arg Leu Val Arg Phe Leu Phe Tyr Ala Asn Leu His Gly
            100                 105                 110
Ser Ile Leu Phe Leu Thr Cys Ile Ser Phe Gln Arg Tyr Leu Gly Ile
        115                 120                 125
Cys His Pro Leu Ala Pro Trp His Lys Arg Gly Gly Arg Arg Ala Ala
    130                 135                 140
Trp Leu Val Cys Val Ala Val Trp Leu Ala Val Thr Thr Gln Cys Leu
145                 150                 155                 160
Pro Thr Ala Ile Phe Ala Ala Thr Gly Ile Gln Arg Asn Arg Thr Val
                165                 170                 175
Cys Tyr Asp Leu Ser Pro Pro Ala Leu Ala Thr His Tyr Met Pro Tyr
            180                 185                 190
Gly Met Ala Leu Thr Val Ile Gly Phe Leu Leu Pro Phe Ala Ala Leu
        195                 200                 205
Leu Ala Cys Tyr Cys Leu Leu Ala Cys Arg Leu Cys Arg Gln Asp Gly
    210                 215                 220
Pro Ala Glu Pro Val Ala Gln Glu Arg Arg Gly Lys Ala Ala Arg Met
225                 230                 235                 240
Ala Val Val Val Ala Ala Phe Ala Ile Ser Phe Leu Pro Phe His Ile
                245                 250                 255
Ile Thr Lys Thr Ala Tyr Leu Ala Val Arg Ser Thr Pro Gly Val Pro
            260                 265                 270
Cys Thr Val Leu Glu Ala Phe Ala Ala Ala Tyr Lys Gly Thr Arg Pro
```

```
            275                 280                 285
Phe Ala Ser Ala Asn Ser Val Leu Asp Pro Ile Leu Phe Tyr Phe Thr
290                 295                 300
Gln Lys Lys Phe Arg Arg Pro His Glu Leu Leu Gln Lys Leu Thr
305                 310                 315                 320
Ala Lys Trp Gln Arg Gln Gly Arg
                325

<210> SEQ ID NO 14
<211> LENGTH: 374
<212> TYPE: PRT
<213> ORGANISM: Homo sapiens

<400> SEQUENCE: 14

Met Ala Ala Asn Val Ser Gly Ala Lys Ser Cys Pro Ala Asn Phe Leu
1               5                   10                  15
Ala Ala Ala Asp Asp Lys Leu Ser Gly Phe Gln Gly Asp Phe Leu Trp
            20                  25                  30
Pro Ile Leu Val Val Glu Phe Leu Val Ala Val Ala Ser Asn Gly Leu
        35                  40                  45
Ala Leu Tyr Arg Phe Ser Ile Arg Lys Gln Arg Pro Trp His Pro Ala
    50                  55                  60
Val Val Phe Ser Val Gln Leu Ala Val Ser Asp Leu Leu Cys Ala Leu
65                  70                  75                  80
Thr Leu Pro Pro Leu Ala Ala Tyr Leu Tyr Pro Pro Lys His Trp Arg
                85                  90                  95
Tyr Gly Glu Ala Ala Cys Arg Leu Glu Arg Phe Leu Phe Thr Cys Asn
            100                 105                 110
Leu Leu Gly Ser Val Ile Phe Ile Thr Cys Ile Ser Leu Asn Arg Tyr
        115                 120                 125
Leu Gly Ile Val His Pro Phe Phe Ala Arg Ser His Leu Arg Pro Lys
    130                 135                 140
His Ala Trp Ala Val Ser Ala Ala Gly Trp Val Leu Ala Ala Leu Leu
145                 150                 155                 160
Ala Met Pro Thr Leu Ser Phe Ser His Leu Lys Arg Pro Gln Gln Gly
                165                 170                 175
Ala Gly Asn Cys Ser Val Ala Arg Pro Glu Ala Cys Ile Lys Cys Leu
            180                 185                 190
Gly Thr Ala Asp His Gly Leu Ala Ala Tyr Arg Ala Tyr Ser Leu Val
        195                 200                 205
Leu Ala Gly Leu Gly Cys Gly Leu Pro Leu Leu Leu Thr Leu Ala Ala
    210                 215                 220
Tyr Gly Ala Leu Gly Arg Ala Val Leu Arg Ser Pro Gly Met Thr Val
225                 230                 235                 240
Ala Glu Lys Leu Arg Val Ala Ala Leu Val Ala Ser Gly Val Ala Leu
                245                 250                 255
Tyr Ala Ser Ser Tyr Val Pro Tyr His Ile Met Arg Val Leu Asn Val
            260                 265                 270
Asp Ala Arg Arg Arg Trp Ser Thr Arg Cys Pro Ser Phe Ala Asp Ile
        275                 280                 285
Ala Gln Ala Thr Ala Ala Leu Glu Leu Gly Pro Tyr Val Gly Tyr Gln
    290                 295                 300
Val Met Arg Gly Leu Met Pro Leu Ala Phe Cys Val His Pro Leu Leu
305                 310                 315                 320
Tyr Met Ala Ala Val Pro Ser Leu Gly Cys Cys Cys Arg His Cys Pro
```

```
                        325                 330                 335
Gly Tyr Arg Asp Ser Trp Asn Pro Glu Asp Ala Lys Ser Thr Gly Gln
                340                 345                 350

Ala Leu Pro Leu Asn Ala Thr Ala Pro Lys Pro Ser Glu Pro Gln
            355                 360                 365

Ser Arg Glu Leu Ser Gln
    370

<210> SEQ ID NO 15
<211> LENGTH: 342
<212> TYPE: PRT
<213> ORGANISM: Homo sapiens

<400> SEQUENCE: 15

Met Gln Ala Val Asp Asn Leu Thr Ser Ala Pro Gly Asn Thr Ser Leu
1               5                   10                  15

Cys Thr Arg Asp Tyr Lys Ile Thr Gln Val Leu Phe Pro Leu Leu Tyr
            20                  25                  30

Thr Val Leu Phe Phe Val Gly Leu Ile Thr Asn Gly Leu Ala Met Arg
        35                  40                  45

Ile Phe Phe Gln Ile Arg Ser Lys Ser Asn Phe Ile Ile Phe Leu Lys
    50                  55                  60

Asn Thr Val Ile Ser Asp Leu Leu Met Ile Leu Thr Phe Pro Phe Lys
65                  70                  75                  80

Ile Leu Ser Asp Ala Lys Leu Gly Thr Gly Pro Leu Arg Thr Phe Val
                85                  90                  95

Cys Gln Val Thr Ser Val Ile Phe Tyr Phe Thr Met Tyr Ile Ser Ile
            100                 105                 110

Ser Phe Leu Gly Leu Ile Thr Ile Asp Arg Tyr Gln Lys Thr Thr Arg
        115                 120                 125

Pro Phe Lys Thr Ser Asn Pro Lys Asn Leu Leu Gly Ala Lys Ile Leu
    130                 135                 140

Ser Val Val Ile Trp Ala Phe Met Phe Leu Leu Ser Leu Pro Asn Met
145                 150                 155                 160

Ile Leu Thr Asn Arg Gln Pro Arg Asp Lys Asn Val Lys Lys Cys Ser
                165                 170                 175

Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
    210                 215                 220

Gly Val Gly Lys Val Pro Arg Lys Lys Val Asn Val Lys Val Phe Ile
225                 230                 235                 240

Ile Ile Ala Val Phe Phe Ile Cys Phe Val Pro Phe His Phe Ala Arg
                245                 250                 255

Ile Pro Tyr Thr Leu Ser Gln Thr Arg Asp Val Phe Asp Cys Thr Ala
            260                 265                 270

Glu Asn Thr Leu Phe Tyr Val Lys Glu Ser Thr Leu Trp Leu Thr Ser
        275                 280                 285

Leu Asn Ala Cys Leu Asp Pro Phe Ile Tyr Phe Leu Cys Lys Ser
    290                 295                 300

Phe Arg Asn Ser Leu Ile Ser Met Leu Lys Cys Pro Asn Ser Ala Thr
305                 310                 315                 320

Ser Leu Ser Gln Asp Asn Arg Lys Lys Glu Gln Asp Gly Gly Asp Pro
```

Asn Glu Glu Thr Pro Met
            340

<210> SEQ ID NO 16
<211> LENGTH: 333
<212> TYPE: PRT
<213> ORGANISM: Homo sapiens

<400> SEQUENCE: 16

Met Asn Thr Thr Val Met Gln Gly Phe Asn Arg Ser Glu Arg Cys Pro
1               5                   10                  15

Arg Asp Thr Arg Ile Val Gln Leu Val Phe Pro Ala Leu Tyr Thr Val
            20                  25                  30

Val Phe Leu Thr Gly Ile Leu Leu Asn Thr Leu Ala Leu Trp Val Phe
        35                  40                  45

Val His Ile Pro Ser Ser Ser Thr Phe Ile Ile Tyr Leu Lys Asn Thr
    50                  55                  60

Leu Val Ala Asp Leu Ile Met Thr Leu Met Leu Pro Phe Lys Ile Leu
65                  70                  75                  80

Ser Asp Ser His Leu Ala Pro Trp Gln Leu Arg Ala Phe Val Cys Arg
                85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
    130                 135                 140

Phe Ile Trp Phe Phe Leu Phe Phe Ile Ser Leu Pro Asn Thr Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
    290                 295                 300

Glu Lys Leu Pro Cys Met Gln Gly Arg Lys Thr Thr Ala Ser Ser Gln
305                 310                 315                 320

Glu Asn His Ser Ser Gln Thr Asp Asn Ile Thr Leu Gly
                325                 330

<210> SEQ ID NO 17
<211> LENGTH: 338
<212> TYPE: PRT

-continued

<213> ORGANISM: Homo sapiens

<400> SEQUENCE: 17

Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
            20                  25                  30

Phe Ile Ala Gly Ile Leu Leu Asn Gly Val Ser Gly Trp Ile Phe Phe
        35                  40                  45

Tyr Val Pro Ser Ser Lys Ser Phe Ile Tyr Leu Lys Asn Ile Val
    50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
        115                 120                 125

Thr Ser Phe Ile Gln Ser Val Ser Tyr Ser Lys Leu Leu Ser Val Ile
130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Leu Ile Val Phe Tyr Thr Ala
        195                 200                 205

Ile Thr Lys Lys Ile Phe Lys Ser His Leu Lys Ser Ser Arg Asn Ser
210                 215                 220

Thr Ser Val Lys Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
            260                 265                 270

Leu Arg Tyr Met Lys Glu Phe Thr Leu Leu Leu Ser Ala Ala Asn Val
        275                 280                 285

Cys Leu Asp Pro Ile Ile Tyr Phe Phe Leu Cys Gln Pro Phe Arg Glu
    290                 295                 300

Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu

<210> SEQ ID NO 18
<211> LENGTH: 339
<212> TYPE: PRT
<213> ORGANISM: Homo sapiens

<400> SEQUENCE: 18

Met Asn Gly Leu Glu Val Ala Pro Pro Gly Leu Ile Thr Asn Phe Ser
1               5                   10                  15

```
Leu Ala Thr Ala Glu Gln Cys Gly Gln Glu Thr Pro Leu Glu Asn Met
             20                  25                  30

Leu Phe Ala Ser Phe Tyr Leu Leu Asp Phe Ile Leu Ala Leu Val Gly
         35                  40                  45

Asn Thr Leu Ala Leu Trp Leu Phe Ile Arg Asp His Lys Ser Gly Thr
 50                  55                  60

Pro Ala Asn Val Phe Leu Met His Leu Ala Val Ala Asp Leu Ser Cys
 65                  70                  75                  80

Val Leu Val Leu Pro Thr Arg Leu Val Tyr His Phe Ser Gly Asn His
                 85                  90                  95

Trp Pro Phe Gly Glu Ile Ala Cys Arg Leu Thr Gly Phe Leu Phe Tyr
                100                 105                 110

Leu Asn Met Tyr Ala Ser Ile Tyr Phe Leu Thr Cys Ile Ser Ala Asp
            115                 120                 125

Arg Phe Leu Ala Ile Val His Pro Val Lys Ser Leu Lys Leu Arg Arg
        130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
                260                 265                 270

Arg Ile Leu Ala Leu Ala Asn Arg Ile Thr Ser Cys Leu Thr Ser Leu
        275                 280                 285

Asn Gly Ala Leu Asp Pro Ile Met Tyr Phe Phe Val Ala Glu Lys Phe
    290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu

<210> SEQ ID NO 19
<211> LENGTH: 337
<212> TYPE: PRT
<213> ORGANISM: Homo sapiens

<400> SEQUENCE: 19

Met Asp Glu Thr Gly Asn Leu Thr Val Ser Ser Ala Thr Cys His Asp
1               5                   10                  15

Thr Ile Asp Asp Phe Arg Asn Gln Val Tyr Ser Thr Leu Tyr Ser Met
            20                  25                  30

Ile Ser Val Val Gly Phe Phe Gly Asn Gly Phe Val Leu Tyr Val Leu
        35                  40                  45

Ile Lys Thr Tyr His Lys Lys Ser Ala Phe Gln Val Tyr Met Ile Asn
```

```
                50              55              60
Leu Ala Val Ala Asp Leu Leu Cys Val Cys Thr Leu Pro Leu Arg Val
65                  70                  75                  80

Val Tyr Tyr Val His Lys Gly Ile Trp Leu Phe Gly Asp Phe Leu Cys
                    85                  90                  95

Arg Leu Ser Thr Tyr Ala Leu Tyr Val Asn Leu Tyr Cys Ser Ile Phe
                100                 105                 110

Phe Met Thr Ala Met Ser Phe Phe Arg Cys Ile Ala Ile Val Phe Pro
                115                 120                 125

Val Gln Asn Ile Asn Leu Val Thr Gln Lys Lys Ala Arg Phe Val Cys
130                 135                 140

Val Gly Ile Trp Ile Phe Val Ile Leu Thr Ser Ser Pro Phe Leu Met
145                 150                 155                 160

Ala Lys Pro Gln Lys Asp Glu Lys Asn Asn Thr Lys Cys Phe Glu Pro
                165                 170                 175

Pro Gln Asp Asn Gln Thr Lys Asn His Val Leu Val Leu His Tyr Val
                180                 185                 190

Ser Leu Phe Val Gly Phe Ile Ile Pro Phe Val Ile Ile Val Cys
                195                 200                 205

Tyr Thr Met Ile Ile Leu Thr Leu Leu Lys Lys Ser Met Lys Lys Asn
210                 215                 220

Leu Ser Ser His Lys Lys Ala Ile Gly Met Ile Met Val Val Thr Ala
225                 230                 235                 240

Ala Phe Leu Val Ser Phe Met Pro Tyr His Ile Gln Arg Thr Ile His
                245                 250                 255

Leu His Phe Leu His Asn Glu Thr Lys Pro Cys Asp Ser Val Leu Arg
                260                 265                 270

Met Gln Lys Ser Val Val Ile Thr Leu Ser Leu Ala Ala Ser Asn Cys
                275                 280                 285

Cys Phe Asp Pro Leu Leu Tyr Phe Phe Ser Gly Gly Asn Phe Arg Lys
                290                 295                 300

Arg Leu Ser Thr Phe Arg Lys His Ser Leu Ser Ser Val Thr Tyr Val
305                 310                 315                 320

Pro Arg Lys Lys Ala Ser Leu Pro Glu Lys Gly Glu Glu Ile Cys Lys
                325                 330                 335

Val

<210> SEQ ID NO 20
<211> LENGTH: 346
<212> TYPE: PRT
<213> ORGANISM: Homo sapiens

<400> SEQUENCE: 20

Met Glu Arg Lys Phe Met Ser Leu Gln Pro Ser Ile Ser Val Ser Glu
1               5                   10                  15

Met Glu Pro Asn Gly Thr Phe Ser Asn Asn Ser Arg Asn Cys Thr
                20                  25                  30

Ile Glu Asn Phe Lys Arg Glu Phe Phe Pro Ile Val Tyr Leu Ile Ile
                35                  40                  45

Phe Phe Trp Gly Val Leu Gly Asn Gly Leu Ser Ile Tyr Val Phe Leu
                50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                85                  90                  95
```

Tyr Tyr Leu Arg Gly Ser Asn Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Asn Ala Cys Phe Asn Pro Leu Leu
290                 295                 300

Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345

<210> SEQ ID NO 21
<211> LENGTH: 1105
<212> TYPE: DNA
<213> ORGANISM: Rattus norvegicus

<400> SEQUENCE: 21
atcctgtaaa ctgtttctac attccctaga cttctgcctt cagccacaag atggatggcc      60
tcgagacagc cctaccgagt ctgactgaca atgcctccct ggcttactct gaacaatgtg     120
gccaagagac gccccctggag aacatgctct tcgcctgctt ctacctcctg gacttcatcc    180
tagcttttgt gggcaacgct ctggccctct ggttttcat ctgggatcac aagtcaggca     240
ctccggccaa cgtgttccta atgcacctgg ctgtggccga cttgtcctgt gtgctggtcc     300
tgcctacccg gttggtttat cacttctctg caatcactg gccttttggg gaaatcccgt     360
gccgactcac tggcttcctc ttctacctga atatgtacgc cagcatctac ttcctcacct     420
gcatcagtgc tgaccggttc ctggccattg tgcacccagt caagtccctc aagcttcgaa     480
gacctctcta tgcccacctg gcctgcgcct tcctgtggat cgtggtggcc gtggctatgg     540
ccccactgct agtgagtccg cagactgtgc agaccaacca cacggttgtc tgcctgcaac     600
tgtaccggga gaaggcctcc catcatgccc tggcttccct ggctgtggct tttaccttcc     660
ccttcatcac cacggtcacc tgctacctgc tgatcattcg cagcctccgc cagggtcccc     720

```
gtatagagaa gcacctcaag aataaagccg tccgcatgat tgctatggtt ctggccatct    780
tcctgatttg ttttgtgccc taccacatcc accgttcagt ctatgtgctt cactaccgcg    840
gtggtgggac ttcgtgctca gctcagcgtg ccctggccct agggaaccgg atcacctcct    900
gcctcaccag cctcaacggg gccctggatc cagtcatgta cttctttgtg gctgagaaat    960
tccgccacgc cttgtgcaac ttgctctgca gcaaacgact cacaggtcct cctcccagct   1020
ttgaagggaa aaccaacgag agctccctga gcgctcggtc tgagctgtga gcccgagctg   1080
ggcgagcctc ggggaggtcc tgtca                                         1105
```

GPR17 MODULATORS, METHOD OF SCREENING AND USES THEREOF

The present invention relates to GPR17-modulating agents, in particular agents able to modify or block GPR17-receptor activity, and their use in the diagnosis and therapy of diseases or dysfunctions involving the same receptor.

BACKGROUND OF THE INVENTION

Extracellular nucleotides are universal and phylogenetically-ancient signalling molecules acting through specific membrane receptors: the seven ligand-gated P2X channels, and the eight G-protein-coupled P2Y receptors (the $P2Y_{1,2,4,6,11,12,13,14}$ receptor subtypes)[1,2]. Endogenous ligands for P2Y receptors include adenine (ATP, ADP), uracil nucleotides (UTP, UDP) and, as more recently recognized, sugar nucleotides (e.g., UDP-glucose and UDP-galactose). Conversely, cysteinyl-leukotrienes (cysLTs) are peptide-conjugated lipid mediators generated by 5-lipoxygenase metabolism of arachidonic acid with established roles in bronchial asthma, acting through the $CysLT_1$ and $CysLT_2$ receptors[3]. Both P2Y receptors and CysLT receptors belong to the ∂ group of the GPCR rhodopsin family (the purin receptor cluster), which also includes the thrombin receptors and a large number of orphan GPCRs[4]. Among receptors in the purin cluster, GPR17[4] is one of the closest receptors to both P2Y and CysLT receptors, with a mean amino acid sequence identity of 31% with the eight recognized P2Y receptors and of 32 and 35% with $CysLT_1$ and $CysLT_2$[4].

STATE OF THE ART

The identification of the nucleotide and amino acid sequences of cysteinyl-leukotriene GPR17 human receptor is reported in GB2360586. Also proposed therein are screening methods that may be used to identify agonists or antagonist modulating cysLT-receptor activity. According to GB2360586, the agents modulating cysLT-receptor activity may be used in the treatment and/or prophylaxis of several disorders.

DESCRIPTION OF THE INVENTION

The invention is based on the finding that GPR17 represents a dualistic receptor responsive to unrelated families of signaling molecules acting through specific G-protein-coupled receptors, namely nucleotides and cysLTs. It has also been found that inhibition of GPR17 by either antagonist ligands or in vivo antisense technology in an animal ischemia model markedly reduces brain damages, indicating that GPR17 represents a common molecular target mediating the neuroinflammatory effects of nucleotides and cysLTs.

The possibility of modulating brain damage by interfering with a receptor responding to two distinct classes of ligands may significantly improve the therapeutic approach to diseases involving an excessive receptor activation, especially cardiovascular, neurodegenerative disorders and kidney ischemia. New chemical entities able to act on both the cysLT and nucleotide component of GPR17, in particular, may prove extremely more effective in preventing brain damage and thus open up entirely new therapeutic strategies.

In a first embodiment, the invention provides a method for the identification of GPR17 modulators other than the leukotrienes or analogues thereof, which essentially comprises the following steps:

1) in vitro contacting GPR17 with a candidate compound, which is preferably a nucleotide derivative or analogue unable to interact with cysLT receptors;
2) determining the receptor response.

As used herein, "GPR17" indifferently indicates the human or rat receptor. The compounds able to bind the receptor and modulate its activity may be further investigated for their therapeutic potential.

The screening method may be applied to the identification of agonists, antagonists, inverse- or partial-agonists. In a preferred embodiment, the screening method is applied to the identification of compounds having receptor-antagonistic activity. In this case, step 1 above is carried out in the presence of a reference compound able to activate the receptor by binding to its nucleotide- or leukotriene-recognition site. Examples of compounds binding to the nucleotide recognition site of GPR17 include UDP, UDP-glucose and UDP-galactose. The assay can be carried out in a cell-based system or using cell preparations or fractions. Preferably, the pharmacological characterization of the receptor is carried out using the $[^{35}GTP]\gamma S$ binding assay or the functional calcium imaging assay.

In the $[^{35}GTP]\gamma S$ assay, upon agonist-binding the receptor undergo a conformational change which induces activation of the G-proteins responsible for signal-transduction. GPR17 activation can be assessed by testing the ability of exogenously added ligands to increase $[^{35}GTP]\gamma S$ binding to purified membranes. In 1321N1 cells (which do not constitutively express any P2Y or CysLT receptors), heterologous hGPR17 expression induced the appearance of specific concentration-dependent responses to the cysLTs $LTD_4$ and $LTC_4$ and to the uracil nucleotides UDP, UDP-glucose and UDP-galactose. The ligand specificity of the human receptor was also confirmed in COS-7 and HEK-293 cells. Both AR-C69931MX (which has been reported as a selective $P2Y_{12}$ and $P2Y_{13}$ antagonist[10,11,15]), and the selective $P2Y_1$-receptor antagonist MRS2179[7] concentration-dependently inhibited the $[^{35}S]GTP\gamma S$ binding stimulated by UDP-glucose in membranes of cells expressing the human receptor. Conversely, the $CysLT_1$ antagonists montelukast and pranlukast[3,13] concentration-dependently inhibited the activation of human and rat receptors induced by $LTD_4$. The different potencies between the two classes of ligands (nanomolar for cysteinyl leukotrienes and micromolar for nucleotides) suggests that GPR17 can undergo differential activation under specific physiological and pathological conditions. In particular, receptor activation by cysteinyl leukotrienes is believed to occur in physiological conditions, while in conditions of stress and injury the effect of nucleotides becomes important. In the latter situation, in fact, the concentration of nucleotides significantly increases in consequence of their release by hypoxic cells and their production by hydrolysis of nucleic acids in dead cells.

According to a further embodiment, the invention provides the use of GPR17-receptor antagonists for the preparation of a therapeutic agent for the treatment of diseases involving GPR17 activation, particularly neuroprotective, anti-inflammatory and preferably anti-ischemic agents for the treatment of cerebral, cardiac and renal ischemia. The antagonists may be identified with the method according to the invention, or they can be selected from the compounds having purinergic-receptor modulating activity. A comprehensive review of these latter can be found in Jacobson K. et al., "Molecular recognition at purine and pyrimidine nucleotide (P2) receptors", Current Topics in Medicinal Chemistry 2004, vol. 4, pp. 671-686, herein entirely incorporated by reference. According to the invention, the antagonists MRS2179 (N6-methyladenosin-3',5'-bis-phosphate, compound no. 46 in the reference) and AR-C69931-MX (N6-methylthio-ethyl-2-trifluoromethyl-ethylthio-adenosin-5'beta-methylene, γ-dichloromethylene trisphosphate, compound no. 57) are particularly preferred.

The invention further provides the use of combinations or associations of compounds acting on the GPR17-receptor sites respectively involved in the recognition of nucleotides and leukotrienes. The compounds acting on the GPR17-receptor site involved in the recognition of leukotrienes are preferably selected from:

- MK-571, 3-(3-(3-(2-(7-chloro-2-quinolinyl)ethenyl)phenyl)-(3-dimethylamino-3-oxo-propyl)thio)methyl)thio)propanoic acid, described in Jones T R et al., (1989) Pharmacology of L-660, 711 (MK-571): "a novel potent and selective leukotriene D4 receptor antagonist". Can J Physiol Pharmacolo 67:17-28;
- Pranlukast ONO-1078, described in Obata T et al., (1985) New antagonists of leukotrienes: ONO-RS-411 and ONO-RS-347. Adv Prostaglandin Thromboxane Leukot Res 15:229-231;
- the inverse agonists MK-571 and Montelukast, described in Dupre D J et al., (2004) Inverse agonist activity of selected ligands of the cysteinyl-leukotriene receptor 1. J Pharmacol Exp Ther 309: 102-108.

The above bibliographic citations are herein entirely incorporated by reference.

For use in therapy, the GPR17 antagonists can be simultaneously administered, for example in a single pharmaceutical form or preparation, or separately, using different administration forms and routes. Besides the synthetic compounds (or "small molecules") indicated above, the therapeutic approach to diseases involving GPR17 activation can be based on:

- expression vectors comprising the nucleotide sequence encoding the receptor protein, deletion or mutation variants thereof, for example plasmids, viruses or phages containing the regulatory sequences necessary for the correct expression of vector polynucleotide sequences (promoters, enhancers, initiation and termination sequences, polyadenylation sequences and, optionally, translation initiation and termination sequences);
- polypeptides having binding affinity to the receptor, able to modify the purinergic or leukotriene activity thereof, including synthetic oligopeptides, monoclonal or polyclonal antibodies recognizing and binding the GPR17 receptor;
- expression vectors comprising polynucleotides derived from the receptor-encoding sequence and governing the synthesis of antisense RNA;
- synthetic antisense polynucleotides as therapeutic agents. These polynucleotides may include molecules (aptamers) able to interact with the receptor or decoy molecules able to link nuclear proteins or regulatory sequences modulating the receptor expression on genomic DNA.

In an established animal model of permanent ischemic damage (the monolateral middle cerebral artery occlusion in the rat, MCAO), either montelukast or AR-C69931MX (GPR17 antagonists) markedly prevented increase of brain damage determined by Magnetic Resonance Imaging. The same result was observed when the expression of GPR17 was knocked down by utilizing antisense oligonucleotides. Of several antisense oligonucleotides designed on the sequence of rGPR17 mRNA, SEQ ID NO: 1 and SEQ ID NO: 2 (herein also referred to as oligo616 and oligo241, respectively) were able to reduce the in vitro expression of rGPR17 and, when intracerebroventricularly injected in rats, to significantly attenuate infarct size evolution in the lesioned cerebral site.

Therefore, in a particularly preferred embodiment, the invention provides antisense oligonucleotides according to SEQ ID NO: 1 and 2, and the use thereof for the preparation of a therapeutic agent for the treatment of ischemic brain damage.

The oligonucleotides sequences may be chemically modified or conjugated to improve their stability, in vivo delivery and pharmacokinetic profile. For example, the oligonucleotide backbone may be modified to contain 2'-O-(C1-C3) alkylribonucleotides, 2'-deoxyribonucleotides, phosphorothioates, phosphorodithioates, phosphotriesters, aminoalkylphosphotriesters, alkyl phosphonates, phosphinates, phosphoroamidates, thionophosphoroamidates, thionoalkylphosphonates or phosphotriesters groups. Other modifications may involve the sugar moiety, the internucleosidic bond or the purine or pyrimidine bases, e. g. by introducing purines and pyrimidines variously substituted on the heterocyclic rings, for example by alkyl, hydroxy- or halo-alkyl, halogen, hydroxyl, sulfur, amino or aza groups. Moreover, the oligonucleotides of the invention can be conjugated with different groups or functionalities able to increase their activity, distribution or cellular uptake. Such groups or functionalities include lipids, aliphatic chains, poliethilenglycol chains, polyamines and phospholipids.

For use in therapy, the pharmacological agents according to the invention, in particular small molecules, peptides and antisense oligonucleotides, may be suitably formulated together with physiologically acceptable excipients or carriers. Suitable pharmaceutical forms may vary depending on the specific compound or substance and on the administration route. The dosage of active ingredient will be determined on a case by case basis, depending on the severity of the disease to be treated and on the general conditions of the patients.

Suitable pharmaceutical compositions may be prepared following the indications provided in Remington's Pharmaceutical Sciences, XVIII Ed. Mack Publishing Co.

In a further embodiment, the invention relates to a diagnostic composition containing a compound, ligand, peptide, antibody or oligonucleotide able to interact with the purinergic site of the GPR17 receptor, particularly useful for the study of receptor functionality under physiological or pathological conditions.

The invention will be further illustrated by the following examples and by the annexed Figures.

DESCRIPTION OF THE FIGURES

FIG. 1.1 Nucleotide and deduced amino acid sequence of hGPR17. The cloned sequence was 99% identical to that reported in the public database (GeneBank accession No: U33447), with the only exception of a T-to-C nucleotide substitution in position 721, which had no effect on the encoded Aminoacid (Leu). Black triangles and circles indicate potential sites for N-linked glycosylation and phosphorylation, respectively. These sites were identified by utilising CBS Prediction Servers (NetPhos 2.0 and NetNGlyc 1.0Server. Structural analysis for indicated putative TM domain determination of the protein sequences were performed with TMpred software.

FIG. 2.1 (a) Sequence multialignment of hGPR17 with $hP2Y_{1,2,3,4,6,11,12,13,14}$ and CysLT1 and CysLT2 receptors. Sequences were obtained from GenBank. Determination of putative open reading frame was performed with DNA Strider 1.2. BLAST searches were performed through the National Center for Biotechnology Information server. Amino acid sequences were aligned with ClustalX1.8. Dark and light gray shading indicates presence of, respectively, at least 50% identical or homologous residues. Boxes indicate putative TM1-7. (b) Amino acid sequence identity and, (c), similarity (i.e., presence of homologous amino acids) of hGPR17 with known P2Y and CysLT receptors.

FIG. 3.1 Abolition of responses to nucleotides and cys-LTs in membranes of cells pretreated with the Gi protein inhibitor PTX.

1321N1 cells expressing hGPR17 were exposed in culture to either vehicle (empty columns) or 100 ng/ml PTX (black columns) for 18 hours before membrane preparation. [$^{35}$S]GTPγS binding was then measured in the absence (basal) or presence of either nucleotides or cys-LTs, as indicated. Data are the mean of 3 experiments run in triplicate. In membranes preincubated with PTX, responses induced by agonists (black column) were in all cases significantly lower ($P<0.001$) with respect to responses detected with the same compounds in membranes from untreated cells (white columns).

Figure 4:
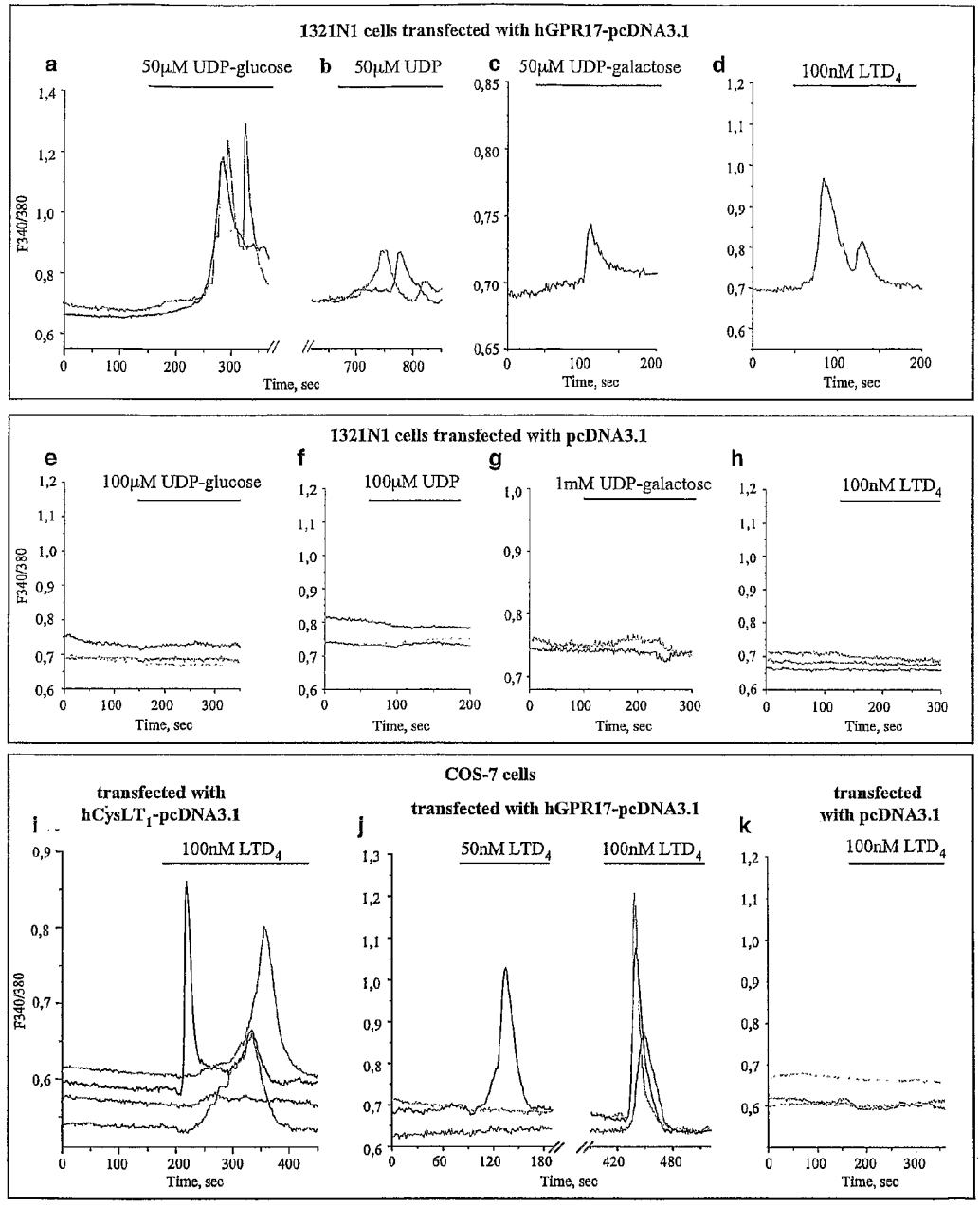

FIG. 4 Single cell calcium imaging in 1321N1 or COS-7 cells expressing hGPR17. Each trace shows response recorded from one single cell. (a-c) Approximately 30% of 1321N1 cells expressing hGPR17 showed responses to uracil nucleotides (mean calcium response to UDP-glucose: ΔF340/380=0.34±0.11, n=7), or (d) to $LTD_4$. (e-h) The same agonists induced no responses in cells transfected with the empty plasmid. (i) Approximately 45% of COS-7 cells transfected with $hCysLT_1$ receptor showed calcium transients to $LTD_4$ (mean calcium response; ΔF340/380=0.3±0.08, n=17). (j) Similar responses were recorded from approximately 50% of COS-7 cells expressing hGPR17 (mean calcium response: ΔF340/380=0.18±0.03, n=22). (k) No responses to $LTD_4$ were recorded in cells transfected with the empty plasmid.

FIG. 4.1 Target sequences of synthesized anti-sense oligonucleotides on rGPR17 mRNA. (a) The various anti-sense sequences were named based on the rat coding sequence (GenBank accession No.: AC112062); black arrows indicate beginning and ending of the coding sequences. All oligonucleotides, including the "scrambled" sequence, were designed as described in Methods. All these sequences were tested in vitro on HEK-293 cells expressing rGPR17 in order to select the most appropriate oligonucleotides to be utilized for the in vivo studies. Two typical experiments are shown in (b), one aimed at assaying oligo616, oligo241 and oligo99, and the other one aimed at assaying oligoSTART and oligoEND, all in comparison with scrambled oligo sequences run in parallel. On day 2 after plating, cells were transfected with pcDNA3.1 containing the construct encoding for rGPR17 together with the neomycin resistance gene, here utilized as a reported gene. The various oligonucleotides described in (a) (all utilized at a 0.3 μM final concentration) were added to cells twice in a small Fugene volume (125 μl): 16 and 40 h after transfection of rGPR17. Twenty-four h after the last Fugene addition, RNA was extracted from cells as described in Methods, and the transcripts for both rGPR17 and the neomycin resistance gene determined as specific RT-PCR amplification products of 1079 and 357 bp, respectively, as indicated. Only oligo616 and, to a lesser extent, oligo241 were able to attenuate rGPR17 mRNA in HEK-293 cells. Based on this, only these 2 antisense oligonucleotides were tested in vivo (see FIG. 5). Similar data have been obtained in 11 different experiments.

Figure 5:
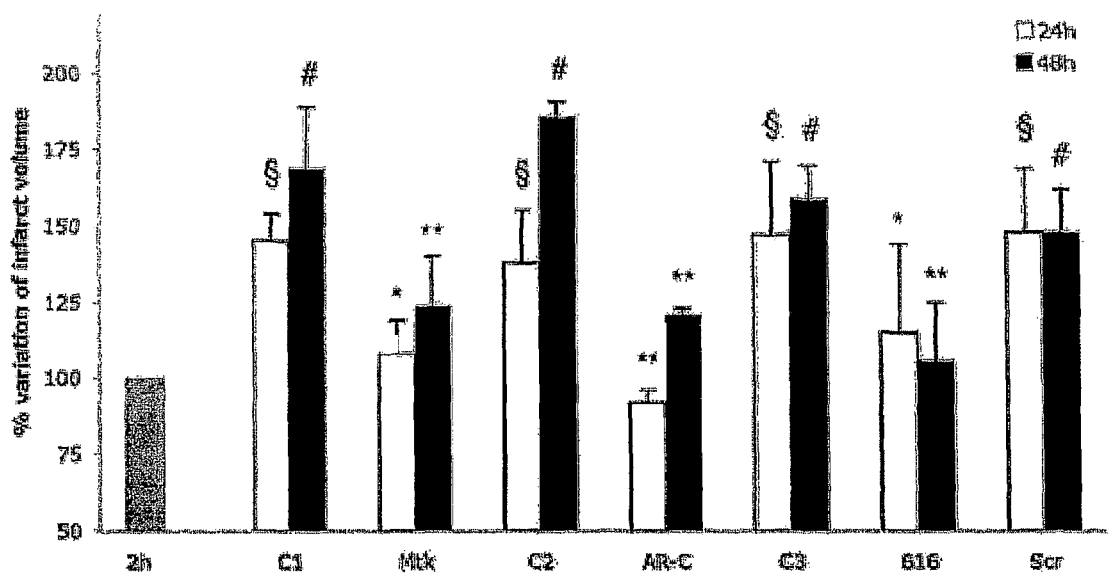

FIG. 5 Effect of montelukast (Mtk), AR-C69931MX (AR-C) and oligo616 on evolution of brain infarct size as determined by MRI at 2, 24, 48 h after MCAo. Quantitative analysis of infarct size volume at 24 and 48 h after MCAo from rats receiving vehicle (C1, n=5) or Mtk (2 mg/kg intravenously, i.v., 10 min after MCAO; n=6); vehicle (C2, n=5) or AR-C (4.5 μg/animal intracerebroventricularly, i.c.v., 10 min after MCAo, n=5), vehicle (C3, n=5) or either oligo616 or scrambled-oligo (400 ng/animal, i.c.v., 48, 24 before and 10 min after MCAo, n=5). Data are expressed as percentage variation of infarct volume at 24 and 48 hours after MCAo compared to 2 h considered as 100% (§ $p<0.05$, # $p<0.01$ vs volume at 2 hr; *$p<0.05$, **$p<0.01$ vs corresponding control evaluated at the same time point).

METHODS

Cell culture and treatments. Human astrocytoma cells (ADF cells), 1321N1, COS-7 and HEK-293 cells were cultured as previously described[11,24]. For [$^{35}$S]GTPγS, $10^6$ 1321N1, COS-7 or HEK-293 cells were seeded on 75 cm$^2$ flasks and transfected by the calcium phosphate precipitation method as previously described[11]. For experiments with anti-sense oligonucleotides (see also below), after plating HEK-293 cells were trasfected with the various oligos in Fugene™. For calcium imaging studies, 1321N1 and COS-7 cells were seeded on 2.4-cm diameter glass coverslips (100×10$^3$ cells). In selected experiments, cells were exposed to 100 ng/ml PTX (Sigma) for 18 h before membrane preparation, to inhibit PTX-sensitive Gi proteins. For treatment of cultured cells with oligonucleotides, 13×10$^4$ HEK-293 cells were seeded on 9 cm$^2$ dishes and treated as described in Supplementary FIG. 4.

Reagents. All culture media and sera were from Celbio. All reagents for RT-PCR, cloning and transfection were from Invitrogen, with the exception of Fugene™, which was from Roche Diagnostics. $LTD_4$ was purchased from Cayman Chemical Co. (Ann Arbor, MI). Anti-sense oligonucleotides were selected according to the general criteria for oligo designing and synthetized by MWG-Biotech AG. In particular, thermodynamic criteria were set according to previous indications[25] and care was taken to avoid internal loop, palindrome of 6 or more base pairs, nucleotides repetition (more then 3 base pairs), and where possible, a AGGG consensus sequence shown to target RNAse degradation was included in the designed oligos (see oligo 616 and 241 in Supplementary FIG. 4)[26]. Oligo antisense sequence was mapped on GPR17 RNA secondary structure predicted using GeneBee service to choose oligo mapping in the loop part of the hairpin; the scrambled oligonucleotide was randomly generated on the basis of the 616oligo. We chose to use unmodified oligonucleotides to avoid possible toxicity, while the stability issue was faced by a multiple delivery experimental design (see FIG. 5 legend and text). Each oligo antisense sequence was challenged with rat Genebank using BLASTA programme to exclude the presence of multiple target sequences in the rat genome. All other reagents were from Sigma-Aldrich.

Total RNA isolation and PCR Analysis. Total RNA was extracted using the TRIZOL® Reagent (Invitrogen) according to manufacturer's instructions. Retrotranscription to cDNA and PCR reactions were carried out as previously described[11].

Cloning and heterologous expression of human and rat GPR17. The following specific oligonucleotide PCR-primers external to the open reading frame (ORF) of the previously reported human receptor sequence (GenBank accession no U33447) were utilized to amplify a 1087 bp product from human astrocytoma ADF cell:

Fw: 5'-GAC-TCC-AGC-CAA-AGC-ATG-AA-3' (SEQ ID NO: 3)

Rw: 5'-GGG-TCT-GCT-GAG-TCC-TAA-ACA-3' (SEQ ID NO: 4)

The amplification product was cloned into a pcDNA3.1 expression vector using the pcDNA3.1/V5-His©TOPO® TA Expression Kit (Invitrogen, Milan, Italy). Interrogation of the rat HTGS database with the nucleotidic sequence of hGPR17 revealed the presence of an highly similar (89% identical) sequence in chromosome 18 supercontig (Genbank accession No.: AC112062). By utilizing specific oligonucleotide primers external to the putative 1020 bp ORF of the rat sequence we also cloned rGPR17 from rat brain. Constructs were verified by sequencing using the Applied Biosystems Terminator cycle sequencing kit. A partial sequence of the mouse ortholog of GPR17 is reported in Genbank (AY255543) and the complete sequence 98% identical to the rat receptor was found in a BAC clone (AC131761) using the rat sequence as a probe in the mouse HTGS database.

[$^{35}$S]GTPγS Binding Assay. 1321N1 cells, COS-7 and HEK-293 cells (control and transfected cells) were homogenized in 5 mM TRIS-HCl, 2 mM EDTA, pH 7.4 and centrifuged at 48000 g for 15 min at 4° C. The resulting pellets (plasma membranes) were washed in 50 mM TRIS-HCl, 10 mM $MgCl_2$, pH 7.4 and stored at −80° C. until used. Measurement of nucleotide-stimulated [$^{35}$S]GTPγS binding to membranes of cells expressing the human or rat GPR17 receptor was performed as previously described[9-11].

Functional calcium imaging assay. Measurements of intracellular calcium concentrations ($[Ca^{2+}]_i$) were carried out as previously described[27]. Forty-eight h after transfection, 1321N1 and COS-7 cells were loaded with 2 μM Fura-2 pentacetoxy methylester in Krebs-Ringer solution, washed and transferred to the recording chamber of an inverted microscope (Axiovert 100; Zeiss, N.Y.) equipped with a calcium imaging unit. Polychrome IV (TILL Photonics, Germany) was used as light source. Fura-2 and EGFP fluorescence images were collected with a PCO Super VGA SensiCam (Axon Instruments, Forest City, Calif.) and analyzed with the Axon Imaging Workbench 2.2 software (Axon Instruments). Images were acquired at 1-4 340/380 ratios/s.

Induction of focal brain ischemia in the rat. Male Sprague-Dawley rats (Charles River) underwent permanent middle cerebral artery occlusion (MCAo) as previously described[28,29]. Drug treatments were as follows: montelukast (2 mg/kg, intravenously, i.v., single bolus of 200 μl in physiological solution) and AR-C69931MX (4.5 μg/animal, intracerebroventricularly, i.c.v., 5 μl in physiological solution) were administered 10 minutes after MCAo. AR-C was utilized here to simply test the involvement of GPR17 in brain ischemia, and, being a very polar molecule which is likely to very poorly permeate the blood brain barrier, it was administered i.c.v. Oligo-616 and oligo-scramble (400 ng in 5 μl of physiological solution) were administered i.c.v three times to each rat 48, 24 h before and 10 minutes after MCAo. Control groups received corresponding vehicle i.c.v.

Magnetic Resonance Imaging analysis. MRI measurements were performed 2, 24 and 48 h after MCAo using a 4.7T, vertical superwidebore magnet of a Bruker AMX3 spectrometer with micro imaging accessory. Animal preparation, image acquisition, trace of the diffusion tensor map computation, ischemic volume determination and progression of the ischemic damage over time was as previously described[30].

Statistical analysis. For [$^{35}$S]GTPγS binding data, analysis and graphic presentation was performed by the non-linear multipurpose curve-fitting computer program Graph-Pad Prism (GraphPad). For calcium imaging, data were normalized to the mean F340/380 increase recorded in control cells. All data are presented as mean±SEM of 4-18 experiments run in triplicate. Statistical analysis was performed by either Student's t test or one-way ANOVA (Scheffe' test). Significance refers to results where $P<0.05$ was obtained.

Results

GPR17: a Close Relative of Both P2Y and CysLT Receptors

Figure 1:
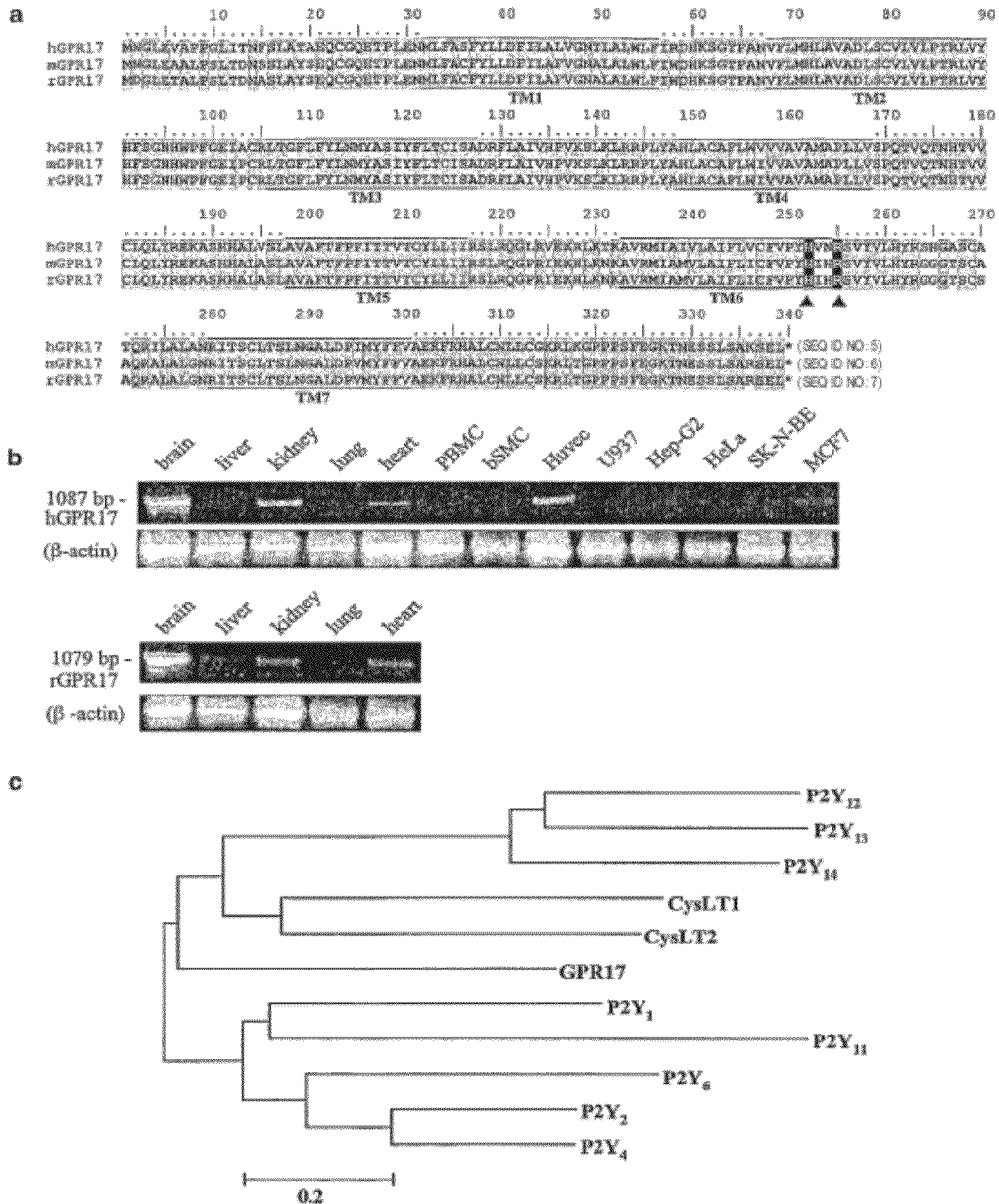
FIG. 1 (a) Multialignment of human, mouse and rat aminoacid GPR17 sequences highlighting the seven TM domains and the conserved H-X-X-R motif in TM6. (b) RT-PCR amplification of the human (1087 bp) or rat (1079 bp) cDNA sequences in brain, kidney, heart, and in human umbilical vein endothelial cells (HUVEC) and breast adenocarcinoma MCF7 cells. No signal was found in peripheral blood mononuclear cells (PBMC), myeloid U937, hepatocellular carcinoma Hep-G2, cervix carcinoma (HeLa) and neuroblastoma SK-N-BE cells. Parallel expression of the house-keeping gene beta-actin is shown. (c) Phylogenetic tree generated with the program Mega 2.1, showing the evolutionary relationships between GPR17 and P2Y and CysLT receptors.
Figure 2:
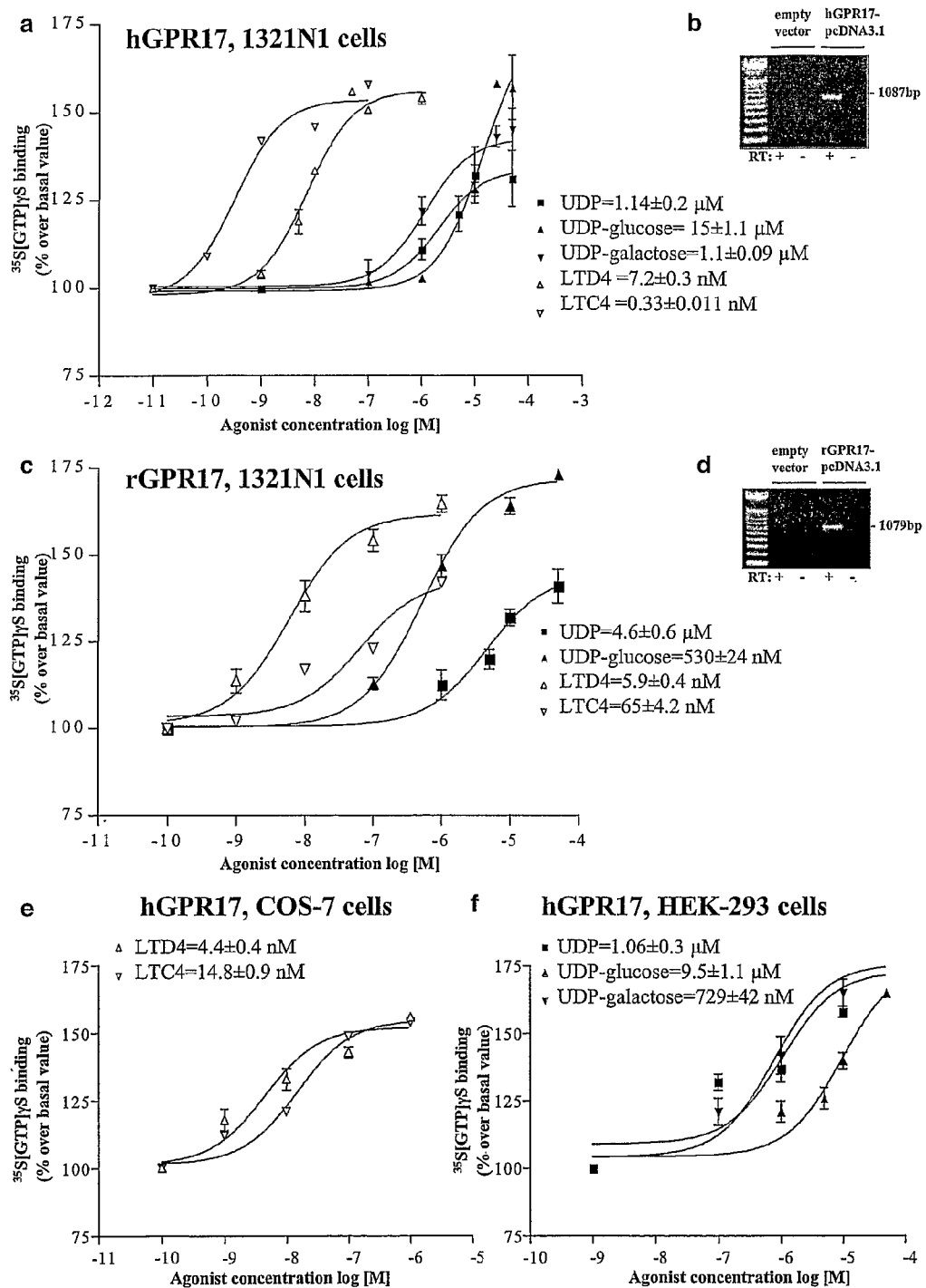
FIG. 2 Determination of GPR17 agonist specificity by [$^{35}$S]GTPγS binding in cells expressing the human and rat receptors. (a) Agonist-response curve to cys-LTs and nucleotides in 1321N1 cells expressing hGPR17, as shown by presence of a specific 1087 bp amplification product (b). No products were detected in samples that did not undergo retrotranscription (RT) (indicated as −RT), nor in cells transfected with the empty vector. (c) and (d), same as (a) and (b) for rGPR17. (e) Responses to cys-LTs in COS-7 cells expressing hGPR17. (f) Responses to nucleotides in HEK-293 cells expressing hGPR17. For each agonist, $EC_{50}$ values are reported. Each point in graphs represents the mean±SD of triplicate determinations from 4-10 independent experiments.

In search for the natural ligand of GPR17, we first cloned and analyzed the coding sequences from the human and rat receptors. The previously unidentified rat hortholog displayed a 89% aminoacid identity with the human sequence (FIG. 1a; FIG. 1.1). The hydropathic profile of deduced putative proteins was consistent with the typical seven transmembrane (7TM) structure of a GPCR (ibidem). Multialignment of rat, mouse and human proteins showed almost complete overlapping of TM3, TM6 and TM7 and conservation of a typical amino acid motif in TM6 (H-X-X-R) that is also present in all known P2Y and CysLT receptors and has been proposed (at least for nucleotide receptors) to be essential for binding to endogenous ligands[5-7] (FIG. 1a). In line with previous tissue distribution data[8], both human and rat GPR17 showed highest expression levels in brain, followed by kidney and heart, with no significant expression in liver and lung (FIG. 1b); hGPR17 mRNA was also found in some of the cell lines tested (see FIG. 1 legend). Identity and similarity of hGPR17 to the known P2Y and CysLT receptors is shown in FIG. 2.1. Similarity was highest with $P2Y_1$ (56%), followed by $CysLT_2$ (54%), $CysLT_1$ (53%), $P2Y_4$ (53%), $P2Y_2$ (52%), $P2Y_{11}$ (50%), $P2Y_{13}$ (49%), $P2Y_{14}$ (48%), $P2Y_{12}$ (47%), $P2Y_6$ (45%). The phylogenetic relationships among these receptors are shown in FIG. 1c. As expected, $CysLT_1$ and $CysLT_2$ receptors cluster together, whereas P2Y receptors cluster in two phylogenetically-distinct subgroups, one encompassing P2Y$_{1,2,4,6,11}$ and the other one encompassing P2Y$_{12,13,14}$[2]. GPR17 is located at an intermediate position between the P2Y$_{12,13,14}$ subgroup and the CysLT$_1$ and CysLT$_2$ group. Thus, its ligand specificity cannot be predicted simply based on its phylogenetic position and remains unknown (FIG. 1c).

Functional Characterization Unveils the Dual Pharmacology of GPR17

Figure 3:
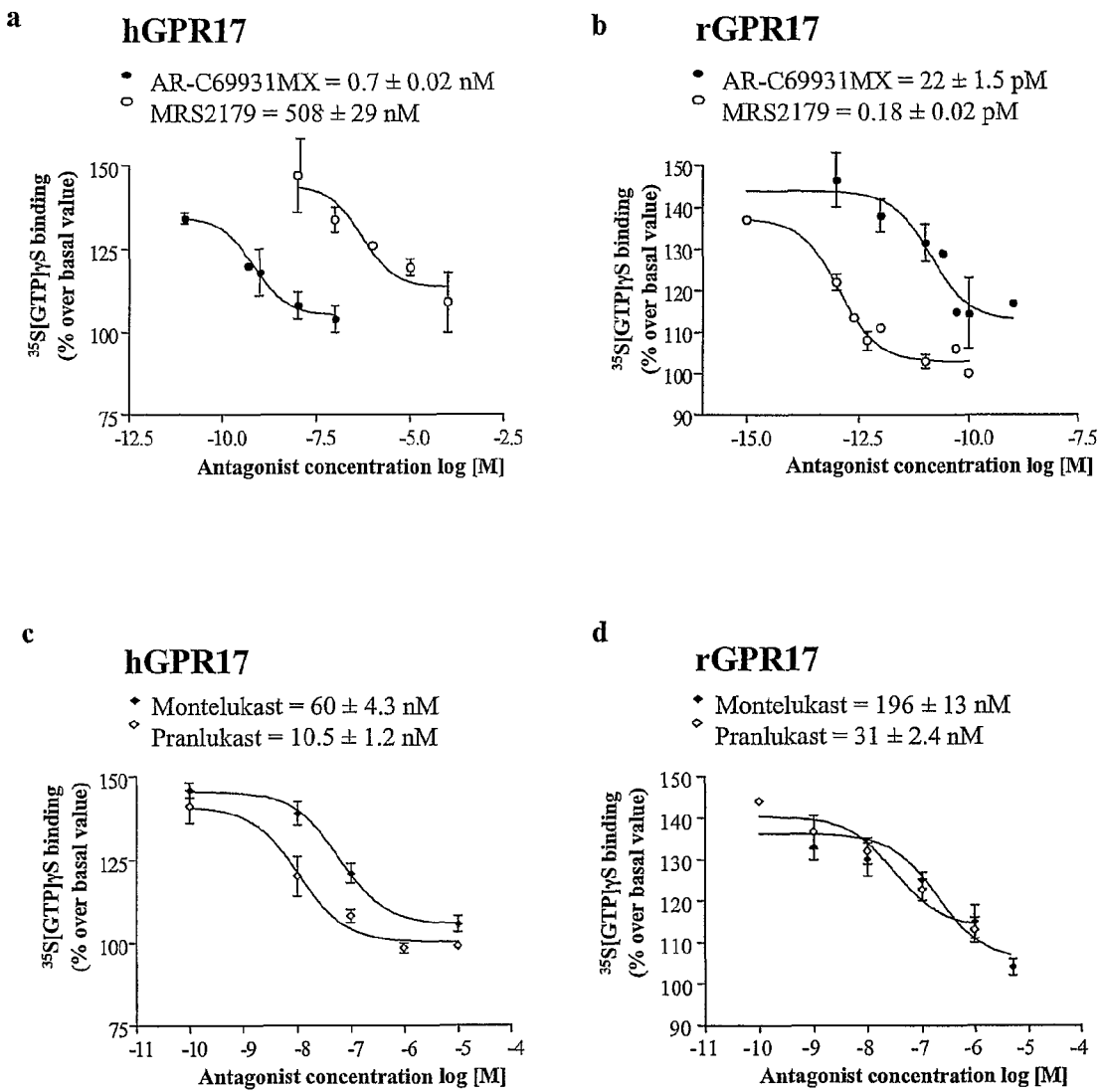
FIG. 3 Effect of P2Y and $CysLT_1$ receptor antagonists on activation of recombinant GPR17 in the [$^{35}$S]GTPγS binding assay. (a) Antagonism of UDP-glucose stimulation of [$^{35}$S]GTPγS binding by the indicated P2Y antagonists in 1321N1 cells expressing the human receptor. (b) same as in (a), in 1321N1 cells expressing the rat receptor. (c) Antagonism of $LTD_4$ stimulation of [$^{35}$S]GTPγS binding by indicated $CysLT_1$ antagonists in 1321N1 cells expressing the human receptor. (d) same as in (c) in 1321N1 cells expressing the rat receptor. Each point in graphs represent the mean±SD of triplicate determinations from 4-7 independent experiments. For each antagonist, $IC_{50}$ values are reported.

To identify the endogenous ligand of GPR17, the cDNAs from human and rat GPR17 were cloned into the mammalian expression vector pcDNA3.1 and transfected in 1321N1, COS-7 and HEK-293 cells for functional characterization. GPR17 activation was assessed by testing the ability of exogenously-added ligands to increase [$^{35}$S]GTPγS binding to purified membranes obtained from transfected cells[9-11]. In 1321N1 cells (which do not constitutively express any functional P2Y or CysLT receptors[12] (Rovati G E & Abbracchio M P, unpublished observations), heterologous hGPR17 expression (FIG. 2b) induced the appearance of specific concentration-dependent responses to the cysLTs LTD$_4$ and LTC$_4$ (with a rank order of potency of LTC$_4$>>LTD$_4$), and to the uracil nucleotides UDP, UDP-glucose and UDP-galactose (with a rank order of potency of UDP-galactose=UDP>UDP-glucose) (FIG. 2a). No other nucleotides or nucleosides (i.e., ATP, ADP, 2-methyl-thio-ADP, UTP, α,βmethylenATP and guanosine, all tested at 10 and 50 μM concentrations) had any effect. Thus, the agonist response profile of GPR17 to cysLTs is different from that of both CysLT$_1$ and CysLT$_2$[3,13], and, for nucleotides, is intermediate between P2Y$_6$ and the P2Y$_{14}$ receptor[1,2]. Interestingly, the concentrations giving half-maximal response (EC$_{50}$) for agonist-stimulation of GPR17 were in agreement with the characteristics of already known CysLT and P2Y receptors[1,3,13], i.e., in the nanoMolar (nM) range for cys-LTs and in μMolar (μM) range for uracil nucleotides (FIG. 2; see also Table 1). This suggests that GPR17 may respond only to cys-LTs, or to both cys-LTs and nucleotides, depending upon different ligand concentrations reflecting specific pathophysiological conditions (see also below). In a similar way, transfection of the newly-cloned rat receptor in 1321N1 cells resulted in rGPR17 expression (FIG. 2d) and appearance of specific responses to nM LTD$_4$ and LTC$_4$ and to μM UDP and UDP-glucose (FIG. 2c). However, interesting differences could be detected by comparing the pharmacological response profiles of the human and rat receptors. At variance from the human receptor, at the rat receptor UDP-glucose was more potent than UDP, and UDP-galactose induced no effect; moreover, the relative potency of cys-LTs was inverted, with LTD$_4$ approximately 10-fold more potent than LTC$_4$ (FIG. 2 and Table 1). The ligand specificity of the human receptor was also confirmed in COS-7 and HEK-293 cells. Transfection in COS-7 cells (which constitutively do not respond to cys-LTs[13]) induced responses to LTD$_4$ and LTC$_4$ (FIG. 2e). COS-7 cells do express several P2Y receptors[14] (Fumagalli M, Verderio C and Abbracchio M P, unpublished observations), so the "purinergic" component of GPR17 could not be studied in these cells. Transfection of hGPR17 in HEK-293 cells also induced responses to UDP, UDP-glucose and UDP-galactose, with a rank order of potency and EC$_{50}$ values similar to those observed in 1321N1 cells (FIG. 2f; Table 1). In either cell system, no responses were ever observed in cells transfected with corresponding empty vectors (data not shown). The specificity of GPR17 responses were also challenged by assessing the ability of some purinergic and leukotriene receptor antagonists to counteract the increase of [$^{35}$S]GTPγS binding evoked by nucleotides and cys-LTs in 1321N1 cells expressing either the human or rat receptor. Both AR-C69931MX (which has been reported as a selective P2Y$_{12}$ and P2Y$_{13}$ antagonist[10,11,15]), and the selective P2Y$_1$-receptor antagonist MRS2179[7] concentration-dependently inhibited the [35S]GTPγS binding stimulated by 50 μM UDP-glucose in membranes of cells expressing the human receptor, with concentrations giving half-maximal inhibition (IC$_{50}$) in the nM range (FIG. 3a; Table 1). These same antagonists also inhibited the effects induced by 50 μM UDP-glucose on the rat receptor (FIG. 3b; Table 1). However, both antagonists were significantly more potent in inhibiting UDP-glucose-induced activation of the rat receptor (FIG. 3b; Table 1), as shown by IC$_{50}$ values in the pMolar (pM) range (FIG. 3b). Moreover, at variance from the human receptor, on rGPR17, MRS2179 was more potent than AR-C69931MX (ibidem). These species differences, together with the differences in agonist-response profile reported above for human and rat GPR17 (FIG. 2) have to be taken into account when using rodent animals as models for preclinical studies aimed at identifying selective modulators of the pathophysiological functions of GPR17. Conversely, the CysLT$_1$ antagonists montelukast and pranlukast[3,13] concentration-dependently inhibited the activation of human (FIG. 3c) and rat receptors induced by 100 nM LTD$_4$, with IC$_{50}$ values in the nM range and similar relative potencies (FIG. 3d; see also Table 1). The demonstration that GPR17 can bind to ligands known to act as selective antagonists only at some P2Y or CysLT receptor subtypes is consistent with its phylogenetic position with respect to more recent members of the "purin cluster". The ability to bind to these ligands may have been progressively lost in parallel with the evolution towards phylogenetically more recent receptors. Because both P2Y[2,11,12] and CysLT receptors[3,13] may couple to G proteins of the Gi subfamily, to evaluate the involvement of this class of G-proteins, we preincubated 1321N1 cells expressing hGPR17 with pertussis toxin (PTX) which inactivates Gi proteins, prior to membrane preparation and [$^{35}$S] GTPγS binding. PTX strongly inhibited [$^{35}$S]GTPγS binding stimulated by either UDP, UDP-galactose, UDP-glucose or LTD$_4$, thus establishing an essential role for this type of G protein in GPR17 responses (FIG. 3.1). Finally, based on data demonstrating that both P2Y and CysLT receptors can also couple to phospholipase C and increase intracellular calcium [Ca$^{2+}$]$_i$[2,3,13], agonist response specificity of GPR17 was also investigated by single cell calcium imaging. Expression of hGPR17 in 1321N1 cells induced rises of [Ca$^{2+}$]$_i$ upon application of either UDP-glucose (FIG. 4a), UDP (FIG. 4b), UDP-galactose (FIG. 4c) or LTD$_4$ (FIG. 4d), although only in approximately 30% of cells. No response was observed in cells transfected with the empty vector (FIG. 4e-h). Expression of hGPR17 in COS-7 cells induced a [Ca$^{2+}$]$_i$ transient to LTD$_4$ in approximately 50% of cells (FIG. 4j); these responses were similar to those observed in approximately 45% of cells transfected with hCysLT$_1$ receptor, here utilized as a positive control (FIG. 4i). No responses were detected in COS-7 cells transfected with the empty plasmid (FIG. 4k).

TABLE 1

| Agonist or antagonist | 1321N1 cells expressing human GPR17 EC$_{50}$ or IC$_{50}$ ± SEM | 1321N1 cells expressing rat GPR17 EC$_{50}$ or IC$_{50}$ ± SEM |
| --- | --- | --- |
| UDP (agonist) | 1.14 ± 0.2 μM | 4.6 ± 0.6 μM |
| UDP-glucose (agonist) | 15 ± 1.1 μM | 530 ± 24 nM |
| UDP-galactose (agonist) | 1.1 ± 0.09 μM | No effect |

TABLE 1-continued

| Agonist or antagonist | 1321N1 cells expressing human GPR17 EC$_{50}$ or IC$_{50}$ ± SEM | 1321N1 cells expressing rat GPR17 EC$_{50}$ or IC$_{50}$ ± SEM |
|---|---|---|
| LTD (agonist) | 7.2 ± 0.3 nM | 5.9 ± 0.4 nM |
| LTC (agonist) | 0.33 ± 0.011 nM | 65 ± 4.2 nM |
| AR-C69931MX (antagonist) | 0.7 ± 0.02 nM | 22 ± 1.5 pM |
| MRS 2179 (antagonist) | 508 ± 29 nM | 0.18 ± 0.02 pM |
| Montelukast (antagonist) | 60 ± 4.3 nM | 196 ± 13 nM |
| Pranlukast (antagonist) | 10.5 ± 1.2 nM | 31 ± 2.4 nM |

Table 1. Potency of various ligands on [$^{35}$S]GTPγS binding to membranes obtaind from 1321N1 cells-transfected with human or rat GPR17. This table summarized the EC$_{50}$ and IC$_{50}$ values for agonists and antagonists respectively, of the various ligand tested in vitro on the recombinant human or rat GPR17, upon expression in 1321N1 cells. All data represent the mean of triplicate determinations from 4-9 independent experiments.

Inhibition of GPR17 Prevents Evolution of Ischemic Brain Damage

In order to characterize the pathophysiological roles of GPR17, based on data suggesting massive accumulation of both cys-LTs and nucleotides in traumatic and ischemic tissues (Burnstock & Knight, 2004; Ciceri et al., 2001, Ohtsuki et al., 1995) and also based on our previous results demonstrating restricted receptor expression in organs that typically undergo ischemic damage (FIG. 1b), we tested the involvement of GPR17 in brain ischemia by utilizing an established animal model of permanent ischemic damage (the monolateral middle cerebral artery occlusion in the rat, MCAO). As expected, Magnetic Resonance Imaging (MRI) of developing damage in the same living animals at 2, 24 and 48 h after MCAo showed that, in control (vehicle-treated) rats, brain infarct volume increased dramatically between 2 and 48 h in the lesioned hemisphere with respect to the controlateral unlesioned side (see Control animals indicated as C1, C2 and C3 in FIG. 5). In vivo treatment of ischemic animals with either montelukast or AR-C69931MX (proved to be effective antagonists of GPR17 in heterologous expression systems in vitro, see FIG. 3), administered 10 min after MCAo (see legend for details) markedly prevented increase of damage with respect to 2 h (FIG. 5), suggesting a contribution of GPR17 to development of ischemic injury. However, since montelukast and AR-C69931MX are also potent antagonists at CysLT$_1$ and P2Y$_{12,13}$ receptors, respectively[3,10,11,15] and some of these receptors are expressed in rat brain (ibidem), to prove the specific involvement of GPR17 in prevention of brain damage, we selectively knocked-down the expression of GPR17 in vivo by utilizing an anti-sense oligonucleotide strategy[18] which has been proven to very efficiently and specifically down-regulate the expression of several other GPCRs in the brain[19,20]. To do so, several anti-sense oligonucleotides have been designed on the sequence of rGPR17 mRNA (indicated as oligoSTART, oligo99, oligo241, oligo-616 and oligoEND in FIG. 4.1) and tested for their ability to down-regulate the mRNA for rGPR17 heterologously expressed in vitro in HEK-293 cells. A randomly generated "scrambled" oligonucleotide sequence was utilized in parallel as an internal control. Of all these anti-sense oligonucleotides, only oligo616 and, to a lesser extent, oligo241 were able to reduce the in vitro expression of rGPR17 in the HEK-293 cells (see FIG. 4.1), and were thus selected for the in vivo MCAo study. These oligonucleotides were administered in vivo by employing a multiple delivery experimental protocol. In a similar way to montelukast and AR-C69931MX, repeated intracerebroventricular (i.c.v.) injections (400 ng/animal) of oligo616 to ischemic rats 48 and 24 h before and 10 min after MCAo markedly and significantly attenuated infarct size evolution in the lesioned hemisphere (FIG. 5). A smaller protective effect was observed with oligo241 (data not shown). No effect on the extent of ischemic damage was observed in animals injected with a non-specific "scrambled" oligonucleotide (FIG. 5). In subsequent experiments, a single cumulative (1200 ng/ml) i.c.v. administration of oligo616 given only 10 min after MCAo also resulted in similar protection against brain damage.(data not shown). These data suggest that inhibition of GPR17 by either antagonist ligands or receptor knock-down results in protection against ischemic brain damage, thus confirming a crucial role for this receptor in injury development. This protection can be attained even if receptor inhibition or knock-down is accomplished after (and not before) ischemia is induced, making this receptor a highly relevant biological target for the development of new therapeutic approaches to stroke treatment.

REFERENCES

1. Burnstock, G. & Knight G. E. Cellular distribution and functions of P2 receptor subtypes in different systems. *Rev. Cytol.* 240, 31-304 (2004).
2. Abbracchio, M. P. et al. Characterization of the UDP-glucose receptor (re-named here the P2Y14 receptor) adds diversity to the P2Y receptor family. *Trends Pharmacol. Sci.* 24, 52-55 (2003).
3. Brink, C. et al. International Union of Pharmacology XXX-VII. Nomenclature for leukotriene and lipoxin receptors. *Pharmacol. Rev.* 55, 195-227 (2003).
4. Fredriksson, R., Lagerstrom, M. C., Lundin, L. G. & Schioth, H. B. The G-protein-coupled receptors in the human genome form five main families. Phylogenetic analysis, paralogon groups, and fingerprints. *Mol. Pharmacol.* 63, 1256-72 (2003).
5. Erb, L. et al. Site-directed mutagenesis of P2U purinoceptors. Positively charged amino acids in transmembrane helices 6 and 7 affect agonist potency and specificity. *J. Biol. Chem.* 270, 4185-4188 (1995).
6. Jiang, Q. et al. A mutational analysis of residues essential for ligand recognition at the human P2Y1 receptor. *Mol. Pharmacol.* 52, 499-507 (1997).
7. Jacobson, K. A., Jarvis, M. F. & Williams M. Purine and pyrimidine (P2) receptors as drug targets. *J. Med. Chem.* 45, 4057-4093 (2002).
8. Blasius, R., Weber, R. G., Lichter, P. & Ogilvie, A. A novel orphan G protein-coupled receptor primarily expressed in the brain is localized on human chromosomal band 2q21. *J. Neurochem.* 70, 1357-1365 (1998).
9. Kotani, M. et al. Functional characterization of a human receptor for neuropeptide FF and related peptides. *Br. J. Pharmacol.* 133, 138-44 (2001).
10. Marteau, F. et al. Pharmacological characterization of the human P2Y13 receptor. *Mol. Pharmacol.* 64, 104-12 (2003).
11. Fumagalli, M. et al. Cloning, pharmacological characterisation and distribution of the rat G-protein-coupled P2Y (13) receptor. *Biochem. Pharmacol.* 68, 113-124 (2004).

12. Communi, D. et al. Identification of a novel human ADP receptor coupled to G(i). *J. Biol. Chem.* 276, 41479-41485 (2001).
13. Capra, V. Molecular and functional aspects of human cysteinyl leukotriene receptors. *Pharmacol. Res.* 50, 1-11 (2004).
14. Herold, C. L., Li, Q., Schachter, J. B., Harden, T. K. & Nicholas, R. A. Lack of nucleotide-promoted second messenger signalling responses in 1321N1 cells expressing the proposed P2Y receptor, p2y7. *Biochem. Biophys. Res. Commun.* 235, 717-721 (1997).
15. Ingall, A. H. et al. Antagonists of the platelet P2T receptor: a novel approach to antithrombotic therapy. *J. Med. Chem.* 42, 213-220 (1999).
16. Ciceri, P., Rabuffetti, M., Monopoli, A. & Nicosia S. Production of leukotrienes in a model of focal cerebral ischaemia in the rat. *Br. J. Pharmacol.* 133, 1323-1329 (2001).
17. Ohtsuki, T. et al. Reperfusion induces 5-lipoxygenase translocation and leukotriene C4 production in ischemic brain. *Am. J. Physiol.* 268, H1249-H1257 (1995).
18. Stein, C. A. The experimental use of antisense oligonucleotides: a guide for the perplexed. *J. Clin. Invest.* 108, 641-644 (2001).
19. Tepper, J. M., Sun, B. C., Martin, L. P. & Creese I. Functional roles of dopamine D2 and D3 autoreceptors on nigrostriatal neurons analyzed by antisense knockdown in vivo. *J. Neurosci.* 17, 2519-2530 (1997).
20. Van Oekelen, D., Luyten, W. H. & Leysen, J. E. Ten years of antisense inhibition of brain G-protein-coupled receptor function. *Brain Res. Brain Res. Rev.* 42, 123-42 (2003).
21. Kenakin, T. P., Bond, R. A. & Bonner, T. I. Definition of pharmacological receptors. *Pharmacol. Rev.* 44, 351-362 (1992).
22. Kenakin, T. Principles: receptor theory in pharmacology. *Trends Pharmacol. Sci.* 25, 186-92 (2004).
23. Mellor, E. A., Maekawa, A., Austen, K. F. & Boyce, J. A. Cysteinyl leukotriene receptor 1 is also a pyrimidinergic receptor and is expressed by human mast cells. *Proc. Natl. Acad. Sci. USA.* 98, 7964-9 (2001).
24. Brambilla, R., Ceruti, S., Malorni, W., Cattabeni, F. & Abbracchio, M. P. A novel gliotic P2 receptor mediating cyclooxygenase-2 induction in rat and human astrocytes. *J. Auton. Nerv. Syst.* 81, 3-9 (2000).
25. Matveeva, O. V. et al. Thermodynamic criteria for high hit rate antisense oligonucleotide design. *Nucleic Acids Res.* 31: 4989-9 (2003).
26. Smith, L. et al. Rational selection of antisense oligonucleotide sequences. *Eur J Pharm Sci.* 11: 191-8. (2000).
27. Fumagalli, M. et al. Nucleotide-mediated calcium signalling in rat cortical astrocytes: Role of P2X and P2Y receptors. *Glia* 43, 218-03 (2003).
28. Tamura, A., Graham, D. I., McCulloch, J. & Teasdale, G. M. Focal cerebral ischaemia in the rat: 1. Description of technique and early neuropathological consequences following middle cerebral artery occlusion. *J. Cereb. Blood Flow Metab.* 1, 53-60 (1981).
29. Sironi, L. et al. Treatment with statins after induction of focal ischemia in rats reduces the extent of brain damage. *Arterioscler. Thromb. Vasc. Biol.* 23, 322-7 (2003).
30. Guerrini, U., et al. New insights into brain damage in stroke-prone rats: a nuclear magnetic imaging study. *Stroke* 33, 825-830 (2002).

---

The invention claimed is:

1. A method for the treatment of cerebral, cardiac and renal ischemia in a subject in need thereof, comprising administering to the subject an effective amount of a GPR17 antagonist, wherein the GPR17 antagonist comprises an antisense oligonucleotide selected from SEQ ID NO: 1 and SEQ ID NO: 2.

2. A method for the treatment of ischemic brain damage in a subject in need thereof, comprising administering to the subject an effective amount of an antisense oligonucleotide selected from SEQ ID NO: 1 and SEQ ID NO: 2.

3. A method for the treatment of ischemic brain, heart and renal damage in a subject in need thereof, comprising administering to the subject an effective amount of small interference RNA (siRNA) comprising at least one of SEQ ID NO: 1 and SEQ ID NO: 2.

4. The method of claim 1, wherein the antisense oligonucleotide has been modified to include 2'—O—(C1-C3) alkylribonucleotide, 2'- deoxyribonucleotide, phosphorothioate, phosphorodithioate, phosphotriester, aminoalkylphosphotriester, alkyl phosphonate, phosphinate, phosphoroamidate, thionophosphoroamidate, thionoalkylphosphonate or phosphotriesters groups.

5. The method of claim 1, wherein the antisense oligonucleotide includes purines or pyrimidines substituted with alkyl, hydroxy- or halo-alkyl, halogen, hydroxyl, sulfur, amino or aza groups.

6. The method of claim 1, wherein the antisense oligonucleotide has been conjugated with lipid, aliphatic chain, poliethilenglycol chain, polyamine or phospholipid groups.

7. The method of claim 1, wherein the antisense oligonucleotide is formulated together with a physiologically acceptable excipient or carrier.

8. The method of claim 2, wherein the antisense oligonucleotide has been modified to include 2'—O—(C1-C3) alkylribonucleotide, 2'- deoxyribonucleotide, phosphorothioate, phosphorodithioate, phosphotriester, aminoalkylphosphotriester, alkyl phosphonate, phosphinate, phosphoroamidate, thionophosphoroamidate, thionoalkylphosphonate or phosphotriesters groups.

9. The method of claim 2, wherein the antisense oligonucleotide includes purines or pyrimidines substituted with alkyl, hydroxy- or halo-alkyl, halogen, hydroxyl, sulfur, amino or aza groups.

10. The method of claim 2, wherein the antisense oligonucleotide has been conjugated with lipid, aliphatic chain, poliethilenglycol chain, polyamine or phospholipid groups.

11. The method of claim 2, wherein the antisense oligonucleotide is formulated together with a physiologically acceptable excipient or carrier.

12. The method of claim 3, wherein the antisense oligonucleotide has been modified to include 2'—O—(C1-C3) alkylribonucleotide, 2'- deoxyribonucleotide, phosphorothioate, phosphorodithioate, phosphotriester, aminoalkylphosphotriester, alkyl phosphonate, phosphinate, phosphoroamidate, thionophosphoroamidate, thionoalkylphosphonate or phosphotriesters groups.

13. The method of claim 3, wherein the antisense oligonucleotide includes purines or pyrimidines substituted with alkyl, hydroxy- or halo-alkyl, halogen, hydroxyl, sulfur, amino or aza groups.

14. The method of claim 3, wherein the antisense oligonucleotide has been conjugated with lipid, aliphatic chain, poliethilenglycol chain, polyamine or phospholipid groups.

15. The method of claim 3, wherein the antisense oligonucleotide is formulated together with a physiologically acceptable excipient or carrier.

* * * * *